(12) United States Patent
Bouhadir et al.

(10) Patent No.: US 12,377,156 B2
(45) Date of Patent: *Aug. 5, 2025

(54) COMPOSITIONS AND METHODS FOR TREATMENT OF WOUNDS AND INFLAMMATORY SKIN CONDITIONS

(71) Applicant: Leuvian LLC, Pinecrest, FL (US)

(72) Inventors: Spencer Bouhadir, Lake Worth, FL (US); Jacob J. Miguel, Pinecrest, FL (US); Cristina I. Miguel, Pinecrest, FL (US)

(73) Assignee: NEUVIAN IP HOLDINGS, LLC, Pinecrest, FL (US)

( * ) Notice: Subject to any disclaimer, the term of this patent is extended or adjusted under 35 U.S.C. 154(b) by 13 days.

This patent is subject to a terminal disclaimer.

(21) Appl. No.: 18/600,557

(22) Filed: Mar. 8, 2024

(65) Prior Publication Data

US 2025/0127911 A1  Apr. 24, 2025

Related U.S. Application Data

(60) Provisional application No. 63/592,694, filed on Oct. 24, 2023.

(51) Int. Cl.
| | |
|---|---|
| *A61K 38/00* | (2006.01) |
| *A61K 47/10* | (2017.01) |
| *A61K 47/12* | (2006.01) |
| *A61K 47/36* | (2006.01) |
| *A61K 47/40* | (2006.01) |
| *A61K 47/64* | (2017.01) |
| *A61P 17/02* | (2006.01) |
| *A61P 29/00* | (2006.01) |

(52) U.S. Cl.
CPC .............. *A61K 47/64* (2017.08); *A61K 47/10* (2013.01); *A61K 47/12* (2013.01); *A61K 47/36* (2013.01); *A61K 47/40* (2013.01); *A61P 17/02* (2018.01); *A61P 29/00* (2018.01)

(58) Field of Classification Search
CPC ........ A61K 47/64; A61K 47/10; A61K 47/12; A61K 47/36; A61K 47/40; A61P 17/02; A61P 29/00
See application file for complete search history.

(56) References Cited

U.S. PATENT DOCUMENTS

| | | | |
|---|---|---|---|
| 2014/0309173 A1 | 10/2014 | Dreher | |
| 2017/0319462 A1 | 11/2017 | Marchant et al. | |
| 2018/0280481 A1 | 10/2018 | Foger et al. | |

FOREIGN PATENT DOCUMENTS

| | | | | |
|---|---|---|---|---|
| CN | 110960442 A | * | 4/2020 | ............... A61K 8/64 |
| WO | WO-2014140890 A2 | * | 9/2014 | ......... A61K 31/4172 |
| WO | WO-2017060500 A1 | * | 4/2017 | ............. A61K 33/26 |

OTHER PUBLICATIONS

Venn skincare (https://vennskincare.com/products/concentrate). (Year: 2018).*
Nayak et al. (J. Complement. Integr. Med. Jun. 1, 2016;13(2):129-36) (Year: 2016).*
INCI Decoder (https://incidecoder.com/products/medik8-liquid-peptides-2021). (Year: 2021).*
Translation of CN110960442A publication obtained by Espacenet (Year: 2020).*
Innovative Skin care—https://isclinical.com.my/wp-content/uploads/2016/06/WhitePaper_CopperTripeptide1_July2014_1_.pdf (Year: 2014).*
Bellia et al. "Copper(II) complexes with B-cyclodextrin-homocarnosine conjugates and their antioxidant activity," Inorganica Chimica Acta, vol. 360, Issue 3, Feb. 15, 2007, pp. 945-954.
Zoughaib et al. "Enhanced angiogenic effects of RGD, GHK peptides and copper (II) compositions in synthetic cryogel ECM model," Mater Sci Eng C Mater Biol Appl. Jan. 2021:120:111660.
International Search Report and Written Opinion for PCT/US24/19261 dated Aug. 13, 2024.

* cited by examiner

*Primary Examiner* — Lianko G Garyu
*Assistant Examiner* — Mercy H Sabila
(74) *Attorney, Agent, or Firm* — Bryan Cave Leighton Paisner LLP

(57) ABSTRACT

Provided herein are compositions that are useful in healing wounds and/or treating inflammatory skin conditions comprising (a) a copper-containing peptide; (b) an antioxidant; and (c) a cyclic oligosaccharide-based polymer, where the copper-containing peptide and the antioxidant form a complex. Further provided herein are methods for healing wounds and/or treating inflammatory skin conditions using the compositions of the disclosure.

21 Claims, 7 Drawing Sheets
(7 of 7 Drawing Sheet(s) Filed in Color)

FIG. 3

| Genes | 0 FM | Carnosine |
|---|---|---|
| Wound Healing | | |
| h COL1A2 | | |
| h EGF-1 | | |
| h MMP-1 | | |
| h ELN | | |
| h FLG | | |
| h IGF-1 | | |
| h ACTA2 | | |
| h HAVCR1 | | |
| h IFN-g | | |
| h ANG-2 | | |

- up-regulation
- no change
- Not expressed

COMPOSITIONS AND METHODS FOR TREATMENT OF WOUNDS AND INFLAMMATORY SKIN CONDITIONS

CROSS-REFERENCE TO RELATED APPLICATIONS

The present invention claims benefit to U.S. Provisional Application Ser. No. 63/592,694 filed Oct. 24, 2023, the entire contents of which are incorporated by reference.

BACKGROUND OF THE INVENTION

Mammalian skin comprises an epidermis layer composed mainly of keratinocytes, melanocytes, and Langerhans cells, and a dermis layer composed mainly of fibroblasts. Skin injury and many skin diseases involve inflammation, wherein the cells of the skin release inflammatory molecules. For example, keratinocytes may produce pro-inflammatory cytokines, such as IL-1, TNF-α, and IL-6, and IL-18, among many others. The identification of compounds that can suppress the production of inflammatory molecules in the skin is beneficial towards development of various therapies, such as treatment of wounds and/or treatment of inflammatory skin diseases such as rosacea, eczema, ad dermatitis. In humans and other mammals wound injury triggers an organized complex cascade of cellular and biochemical events that will in most cases result in a healed wound. An ideally healed wound is one that restores normal anatomical structure, function, and appearance on cellular, tissue, organ, and organism levels. Wound healing, whether initiated by trauma, microbes or foreign materials, proceeds via a complex process encompassing a number of overlapping phases, including inflammation, epithelialization, angiogenesis and matrix deposition. Normally, these processes lead to a mature wound and a certain degree of scar formation.

Anti-oxidant compounds may be beneficial toward suppressing expression of inflammatory molecules and thereby aiding in wound healing and/or treating inflammatory skin disease. The skin itself is a barrier, however, to delivery of therapeutic agents to the cells expressing inflammatory molecules. While various skin penetration enhancing compounds are known, many of these compounds have undesirable side effects including skin irritation, and/or toxicity, and many are incompatible with anti-oxidant compounds.

Thus, there is an unmet need for improved wound healing and anti-inflammatory compositions comprising antioxidants that are effective to penetrate the skin and deliver an anti-oxidant ingredient to effect expression of inflammatory molecules.

SUMMARY OF THE DISCLOSURE

An aspect of the disclosure relates to a composition comprising: (a) a copper-containing peptide; (b) an antioxidant; and (c) a cyclic oligosaccharide-based polymer, wherein the copper-containing peptide and the antioxidant form a complex.

In some embodiments, the copper-containing peptide comprises glycyl-L-histidyl-L-lysine copper (GHK-Cu) peptide. In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises L-carnosine.

In some embodiments, the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof. In some embodiments, the cyclic oligosaccharide-based polymer comprises gamma cyclodextrin, optionally a non-crosslinked gamma cyclodextrin.

In some embodiments, the composition comprises GHK-Cu peptide, carnosine, and cyclodextrin. In some embodiments, the wound healing composition comprises GHK-Cu peptide, L-carnosine, and gamma cyclodextrin.

In some embodiments, the complex formed by the copper-containing peptide and the antioxidant is purple in color. In some embodiments, the composition has a pH between 5.5 and 7.3. In some embodiments, the composition has a pH between 6 and 7.

In some embodiments, the complex formed by the copper-containing peptide and the antioxidant is entrapped by the cyclic oligosaccharide-based polymer. In some embodiments, the wound healing composition comprises by weight of the total composition: (a) 0.1%-2% copper-containing peptide; (b) 0.5%-10% antioxidant; and (c) 0.1%-20% cyclic oligosaccharide-based polymer. In some embodiments, the composition comprises by weight of the total composition: (a) 0.1%-2% copper-containing peptide; (b) 0.5%-10% carnosine; and (c) 0.1%-20% cyclodextrin. In some embodiments, the wound healing composition comprises by weight of the total composition: (a) 0.1%-2% GHK-Cu peptide; (b) 0.5%-10% L-carnosine; and (c) 0.1%-20% gamma cyclodextrin.

In some embodiments, the composition further comprises at least one pharmaceutically acceptable carrier or excipient.

In some embodiments, the composition is a patch, a cream, an ointment, a powder, an aerosol spray, or a hydrogel.

Another aspect of the disclosure is directed to a method for healing a wound and/or treating an inflammatory skin condition in a subject comprising administering to the subject in need thereof a wound healing composition comprising: (a) a copper-containing peptide; (b) an antioxidant; and (c) a cyclic oligosaccharide-based polymer, wherein the copper-containing peptide and the antioxidant form a complex.

In some embodiments, the copper-containing peptide comprises glycyl-L-histidyl-L-lysine copper (GHK-Cu) peptide. In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises L-carnosine.

In some embodiments, the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof. In some embodiments, the cyclic oligosaccharide-based polymer comprises gamma cyclodextrin, optionally a non-crosslinked gamma cyclodextrin.

In some embodiments, the composition comprises GHK-Cu peptide, carnosine, and cyclodextrin. In some embodiments, the composition comprises GHK-Cu peptide, L-carnosine, and gamma cyclodextrin.

In some embodiments, the complex formed by the copper-containing peptide and the antioxidant is purple in color. In some embodiments, the composition has a pH between 5.5 and 7.3.

In some embodiments, the complex formed by the copper-containing peptide and the antioxidant is entrapped by the cyclic oligosaccharide-based polymer. In some embodiments, the composition comprises by weight of the total composition: (a) 0.1%-2% copper-containing peptide; (b) 0.5%-10% antioxidant; and (c) 0.1%-20% cyclic oligosaccharide-based polymer. In some embodiments, the composition comprises by weight of the total composition: (a) 0.1%-2% copper-containing peptide; (b) 0.5%-10% carnosine; and (c) 0.1%-20% cyclodextrin. In some embodiments, the composition comprises by weight of the total composition: (a) 0.1%-2% GHK-Cu peptide; (b) 0.5%-10% L-carnosine; and (c) 0.1%-20% gamma cyclodextrin.

In some embodiments, the composition further comprises at least one pharmaceutically acceptable carrier or excipient.

In some embodiments, the composition is a patch, a cream, an ointment, a powder, an aerosol spray, or a hydrogel.

In some embodiments, the composition is administered topically.

In some embodiments, the composition is administered every hour, every two hours, every three hours, every six hours, every twelve hours, every day, every two days, every three days, every five days, every seven days, every ten days, or every fourteen days.

In some embodiments, the wound is a bed sore, an incision, an excision, a laceration, an abrasion, a puncture or a penetrating wound, a surgical wound, a contusion, a hematoma, a crushing injury, a burn ulcer, an acne scar or a shingles rash.

In some embodiments, the composition is used for skin repair. In some embodiments, the wound healing composition is used to repair a skin wound caused by a dermatological treatment (e.g., a chemical peel, a laser treatment or micro needling).

In some embodiments, the method comprises administering a sunscreen in combination with the composition, wherein the composition and the sunscreen can be administered simultaneous or sequentially.

According to some aspects, the present disclosure provides a composition for altering gene expression of a skin cell in a human subject comprising: (a) a copper-containing peptide; (b) an antioxidant; and (c) a cyclic oligosaccharide-based polymer, wherein the copper-containing peptide and the antioxidant form a complex; and wherein the composition is effective to increase the gene expression of one or more of the genes hCOL1A2, hEGF-1, hMMP-1, hELN, hFLG, and hIGF-1.

In some embodiments, the copper-containing peptide comprises glycyl-L-histidyl-L-lysine copper (GHK-Cu) peptide. In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises L-carnosine. In some embodiments, the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof. In some embodiments, the cyclic oligosaccharide-based polymer comprises gamma cyclodextrin. In some embodiments, the gamma cyclodextrin is a non-crosslinked gamma cyclodextrin. In some embodiments, the composition comprises GHK-Cu peptide, carnosine, and cyclodextrin. In some embodiments, the composition comprises GHK-Cu peptide, L-carnosine, and gamma cyclodextrin. In some embodiments, the complex formed by the copper-containing peptide and the antioxidant is purple in color. In some embodiments, the composition has a pH between 5.5 and 7.3. In some embodiments, the complex formed by the copper-containing peptide and the antioxidant is entrapped by the cyclic oligosaccharide-based polymer. In some embodiments, the composition comprises by weight of the total composition: (a) 0.1%-2% copper-containing peptide; (b) 0.5%-10% antioxidant; and (c) 0.1%-20% cyclic oligosaccharide-based polymer. In some embodiments, the composition comprises by weight of the total composition: (a) 0.1%-2% copper-containing peptide; (b) 0.5%-10% carnosine; and (c) 0.1%-20% cyclodextrin. In some embodiments, the composition comprises by weight of the total composition: (a) 0.1%-2% GHK-Cu peptide; (b) 0.5%-10% L-carnosine; and (c) 0.1%-20% gamma cyclodextrin. In some embodiments, the composition comprises at least one pharmaceutically acceptable carrier or excipient. In some embodiments, the composition is delivered by a patch, a cream, an ointment, a powder, an aerosol spray, or a hydrogel. In some embodiments, the composition is effective to treat a wound or inflammatory condition of the skin. In some embodiments, the inflammatory condition of the skin is eczema, rosacea, or combination thereof.

According to some aspects, the present disclosure provides a method for altering gene expression of a human skin cell in a human subject comprising the steps of contacting the human skin cell with a composition comprising: (a) a copper-containing peptide; (b) an antioxidant; and (c) a cyclic oligosaccharide-based polymer, wherein the copper-containing peptide and the antioxidant form a complex; and wherein the gene expression is one or more of the genes hCOL1A2, hEGF-1, hMMP-1, hELN, hFLG, and hIGF-1.

In some embodiments, the copper-containing peptide comprises glycyl-L-histidyl-L-lysine copper (GHK-Cu) peptide. In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises L-carnosine. In some embodiments, the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof. In some embodiments, the cyclic oligosaccharide-based polymer comprises gamma cyclodextrin. In some embodiments, the gamma cyclodextrin is a non-crosslinked gamma cyclodextrin. In some embodiments, the composition comprises GHK-Cu peptide, carnosine, and cyclodextrin. In some embodiments, the composition comprises GHK-Cu peptide, L-carnosine, and gamma cyclodextrin. In some embodiments, the complex formed by the copper-containing peptide and the antioxidant is purple in color. In some embodiments, the composition has a pH between 5.5 and 7.3. In some embodiments, the complex formed by the copper-containing peptide and the antioxidant is entrapped by the cyclic oligosaccharide-based polymer. In some embodiments, the composition comprises by weight of the total composition: (a) 0.1%-2% copper-containing peptide; (b) 0.5%-10% antioxidant; and (c) 0.1%-20% cyclic oligosaccharide-based polymer. In some embodiments, the composition comprises by weight of the total composition: (a) 0.1%-2% copper-containing peptide; (b) 0.5%-10% carnosine; and (c) 0.1%-20% cyclodextrin. In some embodiments, the composition comprises by weight of the total composition: (a) 0.1%-2% GHK-Cu peptide; (b) 0.5%-10% L-carnosine; and (c) 0.1%-20% gamma cyclodextrin. In some embodiments, the composition comprises at least one pharmaceutically acceptable carrier or excipient. In some embodiments, the composition is delivered by a patch, a cream, an ointment, a powder, an aerosol spray, or a hydrogel. In some embodiments, the composition is effective to treat a wound or inflammatory condition of the skin. In some embodiments, the inflammatory condition of the skin is eczema, rosacea, or combination thereof.

According to some aspects, the present disclosure provides a composition for use in altering gene expression of a human skin cell in a human subject the composition comprising: (a) a copper-containing peptide; (b) an antioxidant; and (c) a cyclic oligosaccharide-based polymer, wherein the copper-containing peptide and the antioxidant form a complex; and wherein the gene expression is one or more of the genes hCOL1A2, hEGF-1, hMMP-1, hELN, hFLG, and hIGF-1.

In some embodiments, the copper-containing peptide comprises glycyl-L-histidyl-L-lysine copper (GHK-Cu) peptide. In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises L-carnosine. In some embodiments, the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof. In some embodiments, the cyclic oligosaccharide-based polymer comprises gamma cyclodextrin. In some embodiments, the gamma cyclodextrin is a non-crosslinked gamma cyclodextrin. In some embodiments, the composition comprises GHK-Cu peptide, carnosine, and cyclodextrin. In some embodiments, the composition comprises GHK-Cu peptide, L-carnosine, and gamma cyclodextrin. In some embodiments, the complex formed by the copper-containing peptide and the antioxidant is purple in color. In some embodiments, the composition has a pH between 5.5 and 7.3. In some embodiments, the complex formed by the copper-containing peptide and the antioxidant is entrapped by the cyclic oligosaccharide-based polymer. In some embodiments, the composition comprises by weight of the total composition: (a) 0.1%-2% copper-containing peptide; (b) 0.5%-10% antioxidant; and (c) 0.1%-20% cyclic oligosaccharide-based polymer. In some embodiments, the composition comprises by weight of the total composition: (a) 0.1%-2% copper-containing peptide; (b) 0.5%-10% carnosine; and (c) 0.1%-20% cyclodextrin. In some embodiments, the composition comprises by weight of the total composition: (a) 0.1%-2% GHK-Cu peptide; (b) 0.5%-10% L-carnosine; and (c) 0.1%-20% gamma cyclodextrin. In some embodiments, the composition comprises at least one pharmaceutically acceptable carrier or excipient. In some embodiments, the composition is delivered by a patch, a cream, an ointment, a powder, an aerosol spray, or a hydrogel. In some embodiments, the composition is effective to treat a wound or inflammatory condition of the skin. In some embodiments, the inflammatory condition of the skin is eczema, rosacea, or combination thereof.

According to some aspects, the present disclosure provides the compositions disclosed herein further comprising a topical formulation suitable for application to the body surface selected from the group consisting of a cream, lotion, spray, solution, gel, ointment, paste, plaster, paint, bioadhesive, suspension, and emulsion. According to some aspects, the present disclosure provides a composition as disclosed herein, wherein the composition further comprises a one or more of sunscreen, lotion, balm, shampoo, and moisturizer.

In some embodiments, the compositions disclosed herein comprise GHK peptide, Carnosine, Gamma-Cyclodextrin, Glycerin, Propanediol, Phenoxyethanol, and ethylhexylglycerin. In some embodiments, the compositions disclosed herein comprise 0.4% GHK peptide, 4% Carnosine, 1% Gamma-Cyclodextrin, 1% Citric acid, 2% Glycerin, 10% Propanediol, 0.7% Phenoxyethanol, 0.1% ethylhexylglycerin, and 1% HA. In some embodiments, the compositions disclosed herein comprise 0.2% GHK peptide, 2% Carnosine, 1% Gamma-Cyclodextrin, 0.5% Citric acid, 2% Glycerin, 10% Propanediol, 0.7% Phenoxyethanol, 0.1% ethylhexylglycerin, 1% HA.

In some embodiments, the composition comprises 0.01-4% GHK peptide, 0.2-20% Carnosine, 0.1-10% Gamma-Cyclodextrin, 0.2-8% Glycerin, 0.1-20% Propanediol, 0.1-3% Phenoxyethanol, 0.01-1% ethylhexylglycerin, and 0.1-10% HA.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 3 shows the gene expression changes of human skin cells following treatment with carnosine, which is the main active ingredient of the composition according to certain embodiments disclosed herein.

DETAILED DESCRIPTION

Definitions

Figure 2:
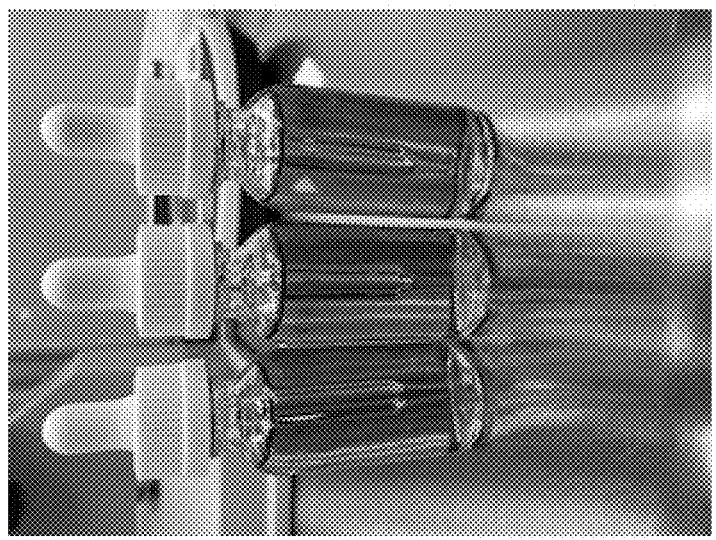
FIG. 2 shows a solution of copper-containing glycyl-L-histidyl-L-lysine copper (GHK-Cu) peptide with distinctive blue color.

The term "about" is used here in conjunction with numeric values to include normal variations in measurements as expected by persons skilled in the art, and is understood have the same meaning as "approximately" and to cover a typical margin of error, such as ±5% of the stated value.

Terms such as "a," "an," and "the" are not intended to refer to only a singular entity, but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination y two or more of the listed elements.

Any amounts (e.g., concentrations) of components in a composition given as a percentage (%) refer to a percentage by weight per volume unless otherwise indicated.

As used herein, a "humectant" refers to a substance having an affinity for water and which provides stabilizing action on the water content of a material.

As used herein, the term "nonionic surfactant" refers to a molecule that acts as an uncharged surfactant. Surfactants are chemical compounds that decrease the surface tension or interfacial tension between two liquids, a liquid and a gas, or a liquid and a solid.

As used herein the term "preservative" refers to any known pharmaceutically acceptable preservative that functions by inhibiting bacteria, fungi, yeast, mold, other microbe. Suitable preservatives include but are not limited to antimicrobial agents. In some embodiments, antimicrobial agents comprise sodium benzoate, paraben, benzyl alcohol, sorbic acid, triclosan, phenoxyisopropanol, diazolidinyl urea, bronopol, Alkyl (C12-22) trimethyl ammonium bromide, Alkyl (C12-22) trimethyl ammonium chloride, Benzalkonium chloride, Benzalkonium bromide, Benzalkonium saccharinate, ethylhexylglycerin, phenoxyethanol, or a combination thereof.

As used herein, "subject" refers to any mammal, including humans, domestic and farm animals, and zoo, sports, or pet animals, such as dogs, horses, cats, sheep, pigs, cows, etc. The preferred subject herein is a human subject, including adults, children, and the elderly.

As used herein, a "wound" refers to an injury to any tissue, including for example, acute, subacute, delayed or difficult to heal wounds, and chronic wounds. Examples of wounds may include both open and closed wounds. Wounds include, for example, bed sores, incisions, excisions, lacerations, abrasions, puncture or penetrating wounds, surgical wounds, contusions, hematomas, crushing injuries, burn ulcer and other types of ulcers. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum).

The compositions and methods of the present invention contemplate treating all wound types, including deep wounds and chronic wounds. The term "chronic wound" refers to a wound that has not healed. In some embodiments, a chronic wound is selected from the group consisting of venous ulcers, pressure sores, vasculitic ulcers, diabetic ulcers and decubitus ulcers. Chronic skin wounds include, for example, pressure ulcers, diabetic ulcers, venous ulcers, vasculitic ulcers, arterial ulcers, and mixed ulcers. The chronic wound may be an arterial ulcer which comprises ulcerations resulting from complete or partial arterial blockage. The chronic wound may be a venous stasis ulcer which comprises ulcerations resulting from a malfunction of the venous valve and the associated vascular disease. The chronic wound may be a trauma-induced ulcer, a diabetic ulcer, or a vasculitic ulcer.

Pressure ulcer: Pressure ulcers may be classified into 4 stages based on AHCPR (Agency for Health Care Policy and Research, U.S. Department of Health and Human Services) guidelines: Stage 1: A stage I pressure ulcer is an observable pressure related alteration of intact skin whose indicators as compared to the adjacent or opposite area on the body may include changes in one or more of the following: skin temperature (warmth or coolness), tissue consistency (firm or boggy feel) and/or sensation (pain, itching). The ulcer appears as a defined area of persistent redness in lightly pigmented skin, whereas in darker skin tones, the ulcer may appear with persistent red, blue, or purple hues. Stage 1 ulceration may include nonblanchable erythema of intact skin and the heralding lesion of skin ulceration. In individuals with darker skin, discoloration of the skin, warmth, edema, induration, or hardness may also be indicators of stage 1 ulceration. Stage 2: stage 2 ulceration may be characterized by partial thickness skin loss involving epidermis, dermis, or both. The ulcer is superficial and presents clinically as an abrasion, blister, or shallow crater. Stage 3: stage 3 ulceration may be characterized by full thickness skin loss involving damage to or necrosis of subcutaneous tissue that may extend down to, but not through, underlying fascia. The ulcer presents clinically as a deep crater with or without undermining of adjacent tissue. Stage 4: stage 4 ulceration may be characterized by full thickness skin loss with extensive destruction, tissue necrosis, or damage to muscle, bone, or supporting structures (e.g., tendon, joint capsule). In certain embodiments compositions and methods of treating a chronic wound are provided where the chronic wound is characterized by one or more of the following AHCPR stages of pressure ulceration: stage 1, stage 2, stage 3, and/or stage 4.

Decubitus ulcers: Decubitus ulcer may arise as a result of prolonged and unrelieved pressure over a bony prominence that leads to ischemia. The wound tends to occur in patients who are unable to reposition themselves to off-load weight, such as paralyzed, unconscious, or severely debilitated persons. As defined by the U.S. Department of Health and Human Services, the major preventive measures include identification of high-risk patients; frequent assessment; and prophylactic measures such as scheduled repositioning, appropriate pressure-relief bedding, moisture barriers, and adequate nutritional status. Treatment options may include for example, pressure relief, surgical and enzymatic debridement, moist wound care, and control of the bacterial load. In certain embodiments compositions and methods of treating a chronic wound are provided wherein the chronic wound is characterized by decubitus ulcer or ulceration which results from prolonged, unrelieved pressure over a bony prominence that leads to ischemia.

Arterial ulcers: Arterial ulcers may be characterized by complete or partial arterial blockage which may lead to tissue necrosis and/or ulceration. Signs of arterial ulcer may include, for example, pulselessness of the extremity; painful ulceration; small, punctate ulcers that are usually well circumscribed; cool or cold skin; delayed capillary return time (briefly push on the end of the toe and release, normal color should return to the toe in about 3 seconds or less); atrophic appearing skin (for example, shiny, thin, dry); and loss of digital and pedal hair. In certain embodiments compositions and methods of treating a chronic wound are provided wherein the chronic wound is characterized by arterial ulcers or ulcerations due to complete or partial arterial blockage.

Venous ulcers: Venous ulcers are the most common type of ulcer affecting the lower extremities and may be characterized by malfunction of the venous valve. The normal vein has valves that prevent the backflow of blood. When these valves become incompetent, the backflow of venous blood causes venous congestion. Hemoglobin from the red blood cells escapes and leaks into the extravascular space, causing the brownish discoloration commonly noted. It has been shown that the transcutaneous oxygen pressure of the skin surrounding a venous ulcer is decreased, suggesting that there are forces obstructing the normal vascularity of the area. Lymphatic drainage and flow also plays a role in these ulcers. The venous ulcer may appear near the medial malleolus and usually occurs in combination with an edematous and indurated lower extremity; it may be shallow, not too painful and may present with a weeping discharge from the affected site. In certain embodiments compositions and methods of treating a chronic wound are provided wherein the chronic wound is characterized by venous ulcers or ulcerations due to malfunction of the venous valve and the associated vascular disease.

Venous stasis ulcers: Venous stasis ulcer may be characterized by chronic passive venous congestion of the lower extremities results in local hypoxia. One possible mechanism of pathogenesis of these wounds includes the impediment of oxygen diffusion into the tissue across thick perivascular fibrin cuffs. Another mechanism is that macromolecules leaking into the perivascular tissue trap growth factors needed for the maintenance of skin integrity. Additionally, the flow of large white blood cells slows due to venous congestion, occluding capillaries, becoming activated, and damaging the vascular endothelium to predispose to ulcer formation. Thus, in certain embodiments compositions and method of treating a chronic wound are provided wherein the chronic wound is characterized by venous stasis ulcers or ulcerations due to chronic passive venous congestion of the lower extremities and/or the resulting local hypoxia.

Diabetic Ulcers: Diabetic patients are prone to foot and other ulcerations due to both neurologic and vascular complications. Peripheral neuropathy can cause altered or complete loss of sensation in the foot and/or leg. Diabetic patients with advanced neuropathy looses all ability for sharp-dull discrimination. Any cuts or trauma to the foot may go completely unnoticed for days or weeks in a patient with neuropathy. A patient with advanced neuropathy looses the ability to sense a sustained pressure insult, as a result, tissue ischemia and necrosis may occur leading to for example, plantar ulcerations. Microvascular disease is one of the significant complication for diabetics which may also lead to ulcerations. In certain embodiments compositions and methods of treating a chronic wound are provided wherein the chronic wound is characterized by diabetic foot ulcers and/or ulcerations due to neurologic and/or vascular complications of diabetes.

Traumatic Ulcers: Formation of traumatic ulcers may occur as a result of traumatic injuries to the body. These injuries include, for example, compromises to the arterial, venous or lymphatic systems; changes to the bony architecture of the skeleton; loss of tissue layers—epidermis, dermis, subcutaneous soft tissue, muscle or bone; damage to body parts or organs and loss of body parts or organs. In certain embodiments, compositions and methods of treating a chronic wound are provided wherein the chronic wound is characterized by ulcerations associated with traumatic injuries to the body.

Burn ulcers: Ulceration may also occur as a result of a burn injury, including 1st degree burn (i.e., superficial, reddened area of skin); 2nd degree burn (a blistered injury site which may heal spontaneously after the blister fluid has been removed); 3rd degree burn (burn through the entire skin and usually require surgical intervention for wound healing); scalding (may occur from scalding hot water, grease or radiator fluid); thermal (may occur from flames, usually deep burns); chemical (may come from acid and alkali, usually deep burns); electrical (either low voltage around a house or high voltage at work); explosion flash (usually superficial injuries); and contact burns (usually deep mid may occur from muffler tail pipes, hot irons and stoves). In some embodiments, compositions and methods of treating a chronic wound are provided wherein the chronic wound is characterized by ulcerations associated with burn injuries to the body.

The term "topical" application refers to application to skin, dermis or tissue site, and application to such tissue sites may include application adjacent to or within the tissue site.

The terms "treat," "treated," or "treating" as used herein refers to therapeutic treatment, cosmetic treatment and/or prophylactic or preventative measures, wherein the object is to prevent or slow down (lessen) an undesired physiological condition, disorder or disease, or to obtain beneficial or desired clinical results. As used herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

As used herein, the term a "therapeutically effective amount" is an amount sufficient to effect beneficial or desired results. A therapeutically effective amount can be administered in one or more doses. The therapeutically effective amount is generally determined by a physician on a case-by-case basis and is within the skill of one in the art. Several factors are typically taken into account when determining an appropriate dosage. These factors include age, sex and weight of the patient, the condition being treated, the severity of the condition and the form of the composition being administered.

The instant disclosure provides compositions and methods for wound healing and tissue regeneration, particularly for treating skin lesions such as wounds. The compositions and methods are useful especially for assisting the process of wound healing, particularly chronic open lesions that are slow to heal or resistant to healing. The compositions and methods also prevent scar formation during wound healing. In some embodiments, the compositions and methods are useful in reducing the grade of a wound, e.g., promoting healing of a Grade IV/III wound to a Grade II/I wound or better. In some embodiments, the compositions and methods show therapeutic effect on the wound after at least two days, three days, four days, five days, six days, or a week of use.

Compositions

The compositions of the present disclosure can be used to treat any disorder, disease, or condition that would benefit from an agent that promotes wound healing and/or reduces swelling, inflammation, and/or scar formation. In some embodiments, the compositions of the present disclosure can be used to treat wounds resulting from surgery or trauma, and wound associated abnormalities in connection with neuropathic, ischemic, microvascular) pathology, pressure over bony area (tailbone (sacral), hip (trochanteric), buttocks (ischial), or heel of the foot), reperfusion injury, and valve reflux etiology and conditions.

In some aspects, the present disclosure provides a delivery system that is effective to penetrate human skin. In some embodiments, the delivery system comprises a penetration-enhancing agent and/or surfactant ingredient or combinations thereof. In certain embodiments, the delivery system is effective to transport one or more active ingredients into the epidermis or dermis.

An aspect of the disclosure is directed to a wound healing composition and/or compositions for treating an inflammatory skin condition comprising: (a) a copper-containing peptide; (b) an antioxidant; and (c) a cyclic oligosaccharide-based polymer, wherein the copper-containing peptide and the antioxidant form a complex.

In some embodiments, the copper-containing peptide comprises glycyl-L-histidyl-L-lysine copper (GEM-Cu) peptide. In some embodiments, the wound healing composition and/or compositions for treating an inflammatory skin condition comprises, by weight of the total composition, 0.1%-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) of copper-containing peptide. In some embodiments, the wound healing composition and/or compositions for treating an inflammatory skin condition comprises, by weight of the total composition, 0.1%-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) GHK-Cu peptide.

In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises carnosine. In some embodiments, the antioxidant comprises anserine. In some embodiments, the antioxidant comprises L-carnosine. In some embodiments, the wound healing composition and/or compositions for treating an inflammatory skin condition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) antioxidant. In some embodiments, the wound healing composition and/or compositions for treating an inflammatory skin condition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) carnosine. In some embodiments, the wound healing composition and/or compositions for treating an inflammatory skin condition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) L-carnosine.

In some embodiments, the wound healing composition and/or compositions for treating an inflammatory skin condition comprises GHK-Cu peptide, carnosine, and cyclodextrin. In some embodiments, the wound healing composition and/or compositions for treating an inflammatory skin condition comprises comprising GHK-Cu peptide, L-carnosine, and gamma cyclodextrin.

In some embodiments, the cyclic oligosaccharide-based polymer comprises an alpha cyclodextrin, beta cyclodextrin, a gamma cyclodextrin, a 2-hydroxypropyl-β-cyclodextrin, a β-cyclodextrin sulfobutylether, hydroxyethyl-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-1-β-cyclodextrin, glocosyl-β-cyclodextrin, maltosyl-β-cyclodextrin or any derivative thereof, and any combination thereof. In some embodiments, the cyclic oligosaccharide-based polymer is non-crosslinked. In some embodiments, the cyclic oligosaccharide-based polymer is crosslinked. In some embodiments, the cyclic oligosaccharide-based polymer is an alkylated derivative. In some embodiments, the wound healing composition and/or compositions for treating an inflammatory skin condition comprises, by weight of the total composition, 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclic oligosaccharide-based polymer. In some embodiments, the wound healing composition and/or compositions for treating an inflammatory skin condition comprises, by weight of the total composition, 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclodextrin or an alkylated derivative thereof. In some embodiments, the wound healing composition and/or compositions for treating an inflammatory skin condition comprises, by weight of the total composition, 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) gamma cyclodextrin or an alkylated derivative thereof.

In some embodiments, the cyclic oligosaccharide-based polymer comprises gamma cyclodextrin. In some embodiments, the gamma cyclodextrin comprises non-crosslinked gamma cyclodextrin. In some embodiments, the gamma cyclodextrin comprises crosslinked gamma cyclodextrin.

In some embodiments, the alpha cyclodextrin has the following chemical formula:

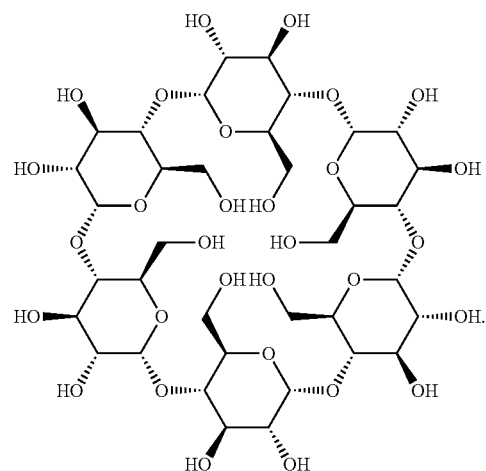 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]1[C@H](O)[C@H]2O)O[C@@H]7CO)O[C@@H]6CO)O[C@@H]5CO)O[C@@H]4CO)O[C@@H]3CO]

In some embodiments, the beta cyclodextrin has the following chemical formula:

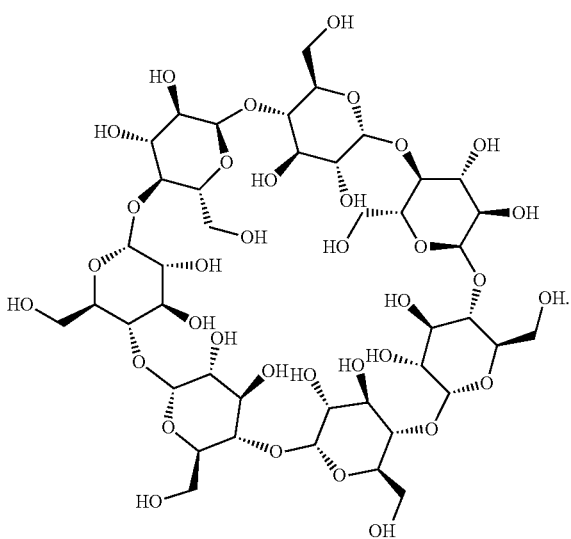 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]1[C@H](O)[C@H]2O)O[C@@H]8CO)O[C@@H]7CO)O[C@@H]6CO)O[C@@H]5CO)O[C@@H]4CO)O[C@@H]3CO]

In some embodiments, the gamma cyclodextrin has the following chemical formula:

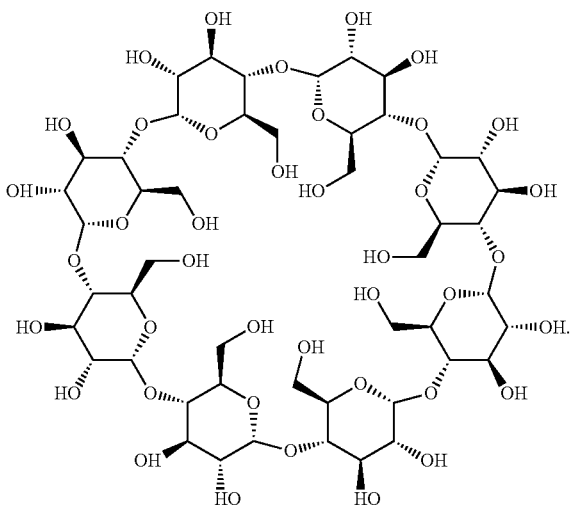 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]9[C@H](O)[C@@H](O)[C@@H](O[C@H]1[C@H](O)[C@H]2O)O[C@@H]9CO)O[C@@H]8CO)O[C@@H]7CO)O[C@@H]6CO)O[C@@H]5CO)O[C@@H]4CO)O[C@@H]3CO]

Figure 1:
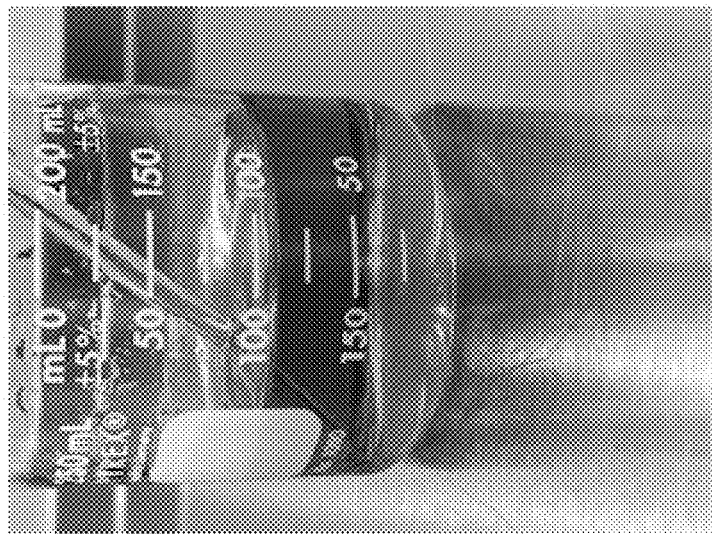
FIG. 1 shows an exemplary serum with distinctive purple color.

In some embodiments, the complex formed by the copper-containing peptide and the antioxidant is purple in color (FIG. 1), while the copper-containing peptide is blue in color (FIG. 2). In some embodiments, the complex formed by GHK-Cu peptide and carnosine is purple in color. In some embodiments, the complex formed by GHK-Cu peptide and L-carnosine is purple in color.

In some embodiments, the composition has a pH between 5.5 and 7.3 (e.g., pH 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3 or any value therebetween). In some embodiments, the composition has a pH between band 7 (e.g., pH 6, 6.1, 6.2, 6.3, 6.4, 6.5, 6.6, 6.7, 6.8, 6.9, 7, or any value therebetween).

In some embodiments, the copper-containing peptide is entrapped by the cyclic oligosaccharide-based polymer. In some embodiments, the GHK-Cu peptide is entrapped by cyclodextrin. In some embodiments, the GHK-Cu peptide is entrapped by gamma cyclodextrin. In some embodiments, the complex formed by the copper-containing peptide and the antioxidant is entrapped by the cyclic oligosaccharide-based polymer. In some embodiments, the complex formed by GHK-Cu peptide and carnosine is entrapped by cyclodextrin. In some embodiments, the complex formed by GHK-Cu peptide and L-carnosine is entrapped by gamma cyclodextrin.

In some embodiments, the wound healing composition and/or compositions for treating an inflammatory skin condition comprises by weight of the total composition: (a) 0.1%-2% copper-containing peptide (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween); (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) antioxidant; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclic oligosaccharide-based polymer.

In some embodiments, the wound healing composition and/or compositions for treating an inflammatory skin condition comprises by weight of the total composition: (a) 0.1%-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) copper-containing peptide; (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) carnosine; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclodextrin.

In some embodiments, the wound healing composition and/or compositions for treating an inflammatory skin condition comprises by weight of the total composition: (a) 0.1%-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) GHK-Cu peptide; (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) L-carnosine; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) gamma cyclodextrin.

In some embodiments, the wound healing composition and/or compositions for treating an inflammatory skin condition further comprises at least one pharmaceutically acceptable carrier or excipient.

In some embodiments, the wound healing composition and/or compositions for treating an inflammatory skin condition further comprises at least one of: a pH buffer; a humectant; a nonionic surfactant; and a preservative.

In some embodiments, the wound healing composition and/or compositions for treating an inflammatory skin condition comprises 0.05%-3% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3%, or any value therebetween) pH buffer. In some embodiments, the wound healing composition and/or compositions for treating an inflammatory skin condition comprises 3%-30% (e.g., 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30%, or any value therebetween) humectant. In some embodiments, the wound healing composition and/or compositions for treating an inflammatory skin condition comprises 5%-15% (5, 5.5, 6, 6.5, 7, 7.5, 8, 8.5, 9, 9.5, 10, 10.5, 11, 11.5, 12, 12.5, 13, 13.5, 14, 14.5, 15%, or any value therebetween) nonionic surfactant. In some embodiments, the wound healing composition and/or compositions for treating an inflammatory skin condition comprises 0.05%-1.5% (e.g., 0.05, 0.1, 0.2, 0.3, 0.4, 0.5, 0.6, 0.7, 0.8, 0.9, 1, 1.1, 1.2, 1.3, 1.4, 1.5, or any value therebetween) preservative.

In some embodiments, the pH buffer comprises at least one of citric acid, magnesium citrate, magnesium sulfate, sodium citrate or sodium sulfate. In some embodiments, the pH buffer comprises citric acid.

In some embodiments, the humectant comprises at least one of an amino acid, aloe vera extract, a fatty acid, hyaluronic acid (HA), collagen, silicone, a disaccharide (e.g., sucrose or trehalose), maltitol, erythrol, sorbitol, glycerin, propanediol, propylene glycol, glycerin or any other glycol/diol. In some embodiments, the humectant comprises glycerin and/or HA. In some embodiments, HA is swapped for any other heavy molecular weight polymer such as collagen or a derivative thereof. In some embodiments, collagen is interchangeable with HA or can be combined with HA, e.g., 0.6% HA combined with 0.5% collagen. In some embodiments, the composition comprises 0.2-5% of HA, 0.2-5% of collagen or derivatives thereof, or 0.2-5% of HA and collagen or a derivative thereof combined. In some embodiments, the wound healing composition and/or compositions for treating an inflammatory skin condition comprises 3-30% (e.g., 3, 4, 5, 6, 7, 8, 9, 10, 11, 12, 13, 14, 15, 16, 17, 18, 19, 20, 21, 22, 23, 24, 25, 26, 27, 28, 29, 30% or any number therebetween) of propanediol, propylene glycol, glycerin or any other glycol/diol, or a combination thereof.

In some embodiments, the nonionic surfactant comprises at least one of tearyl alcohol, cetearyl alcohol, or a combination of both. In some embodiments, the nonionic surfactant comprises tearyl alcohol. In some embodiments, the nonionic surfactant comprises cetearyl alcohol. In some embodiments, the wound healing composition and/or compositions for treating an inflammatory skin condition comprises 3-30% of a nonionic surfactant.

In some embodiments, the preservative comprises at least one of sodium benzoate, paraben, benzyl alcohol, sorbic acid, triclosan, phenoxyisopropanol, diazolidinyl urea, bronopol, Alkyl (C12-22) trimethyl ammonium bromide, Alkyl (C12-22) trimethyl ammonium chloride, Benzalkonium chloride, Benzalkonium bromide, Benzalkonium saccharinate, ethylhexylglycerin, or phenoxyethanol. In some embodiments, the preservative comprises phenoxyethanol or ethylhexylglycerin or both, optionally at 0.5%-1.5% of the composition. In some embodiments, the phenoxyethanol or ethylhexylglycerin can be swapped for parabens or other aromatic alcohols such as benzyl alcohol, optionally at 0.5%-1.5% of the composition.

In some embodiments, the wound healing composition and/or compositions for treating an inflammatory skin condition further comprises at least one of the following constituents: sunflower oil, Tegomuls 90 S, cetyl alcohol, cetyl palmitate, Polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil or distilled water.

In some embodiments, the wound healing composition and/or compositions for treating an inflammatory skin condition further comprises at least one constituent selected from the group consisting of an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, and an antipruritic agent.

In some embodiments, the composition is lyophilized. In some embodiments, the composition is spray dried to form a sterile powder. In some embodiments, the composition is freeze dried onto a wound dressing patch.

In some embodiments, the wound healing composition and/or compositions for treating an inflammatory skin condition is a patch, a cream, an ointment, a powder, an aerosol spray, or a hydrogel. In some embodiments, the wound healing composition and/or compositions for treating an inflammatory skin condition is impregnated into a dressing.

In some embodiments, the wound healing composition and/or compositions for treating an inflammatory skin condition is a patch.

According to certain embodiments, the compositions disclosed herein are in a topical formulation suitable for application to the body surface, such as a cream, lotion, sprays, solution, gel, ointment, paste, plaster, paint, bioadhesive, suspensions, emulsions, or the like, and/or can be prepared so as to contain liposomes, micelles, and/or microspheres. Such a formulation can be used in combination with an occlusive overlayer so that moisture evaporating from the body surface is maintained within the formulation upon application to the body surface and thereafter.

Topical formulations include those in which any other active ingredient(s) is (are) dissolved or dispersed in a dermatological vehicle known in the art (e.g., aqueous or nonaqueous gels, ointments, water-in-oil or oil-in-water emulsions). Constituents of such vehicles can comprise water, aqueous buffer solutions, non-aqueous solvents (e.g., ethanol, isopropanol, benzyl alcohol, 2-(2-ethoxyethoxy) ethanol, propylene glycol, propylene glycol monolaurate, glycofurol or glycerol), oils (e.g., a mineral oil such as a liquid paraffin, natural or synthetic triglycerides, or silicone oils such as dimethicone). Depending, inter alia, upon the nature of the formulation as well as its intended use and site of application, the dermatological vehicle employed can contain one or more components (e.g., when the formulation is an aqueous gel, components in addition to water) selected from the following list: a solubilizing agent or solvent (e.g., a β-cyclodextrin, such as bydroxypropyl, or an alcohol or polyol such as ethanol, propylene glycol or glycerol); a thickening agent (e.g., hydroxyethylceliulose, hydroxypropylcellulose, carboxymethylcellulose or carbomer); a gelling agent (e.g., a polyoxyethylene-polyoxypropylene copolymer); a preservative (e.g., benzyl alcohol, benzalkonium chloride, chlorhexidine, chlorbutol, a benzoate, potassium sorbate or EDTA or salt thereof); and pH buffering agent(s) (e.g., a mixture of dihydrogen phosphate and hydrogen phosphate salts, or a mixture of citric acid and a hydrogen phosphate salt).

A pharmaceutically acceptable carrier can also be incorporated in the formulation of the present disclosure and can be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers. The term "pharmaceutically acceptable" or "pharmaceutically acceptable carrier" is used herein to refer to a compound or composition that can be incorporated into a pharmaceutical formulation without causing undesirable biological effects or unwanted, interaction with other components of the formulation. "Carriers" or "vehicles" as used herein refer to carrier materials suitable for incorporation in a topically applied composition. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue.

According to certain embodiments, the formulations disclosed herein may comprise a film former. A film former, when it dries, forms a protective film over the site of application. The film former inhibits removal of the active ingredient and keeps it in contact with the site being treated. An example of a film former is Flexible Collodion, US P. As described in Remington: The Science and Practice of Pharmacy, 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former can act additionally as a carrier. Solutions that dry to form a film are sometimes referred to as paints. Creams, as is well known in the arts of pharmaceutical formulation, are viscous liquids or semisolid emulsions, either oil-in-water or water-in-oil.

Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which particles, including the active agent, are present in a water or alcohol base. Lotions are usually suspensions of solids, and in some embodiments, comprise a liquid oily emulsion of the oil-in-water type. In some embodiments, lotion formulations are used herein for treating large body areas, because of the ease of applying a more fluid composition. It is generally necessary that the insoluble matter in a lotion be finely-divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize, or preserve the solute. Common examples of solvents used in preparing solutions are ethanol, water, propylene glycol or any other acceptable vehicles. As is well known, gels are semisolid, suspension-type systems. Single-phase gels contain organic macromolecules distributed substantially uniformly throughout the carrier liquid, which is typically aqueous, but also, in some embodiments, contains an alcohol, and, optionally, an oil. In some embodiments, "organic macromolecules," are used, i.e., gelling agents, are cross-linked acrylic acid polymers such as the "carbomer" family of polymers, e.g., carboxypolyalkylenes that can be obtained commercially under the Carbopol trademark. In other embodiments, hydrophilic polymers are used such as polyethylene oxides, polyoxyethylene-polyoxypropylene copolymers and polyvinylalcohol; cellulosic polymers such as hydroxy-propyl cellulose, hydroxyethyl cellulose, hydroxypropyl methylcellulose, hydroxy-propyl methylcellulose phthaiate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof. Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, Pa.: Mack Publishing Co., 1995), at pages 1399-1404, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum.

Enhancers are those lipophilic co-enhancers typically referred to as "plasticizing" enhancers, i.e., enhancers that have a molecular weight in the range of about 150 to 1000, an aqueous solubility of less than about 1 wt. %, in some embodiments less than about 0.5 wt. %, and most in some embodiments less than about 0.2 wt. %. The Hildebrand solubility parameter 6 of plasticizing enhancers is in the range of about 2.5 to about 10, in some embodiments in the range of about 5 to about 10. In some embodiments lipophilic enhancers are fatty esters, fatty alcohols, and fatty ethers. Examples of specific fatty acid esters include methyl laurate, ethyl oleate, propylene glycol nionolaurace, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, in some embodiments, a $C_2$-$C_4$ alkane diol or triol, are substituted with one or two fatty ether substituents. Additional permeation enhancers will be known to those of ordinary skill in the art of topical drug delivery, and/or are described in the pertinent texts and literature. See, e.g., Percutaneous Penetration Enhancers, eds. Smith et al. (CRC Press, 1995) (incorporated herein by reference).

Various other additives can be included in the compositions of the present disclosure in addition to those identified above. These include, but are not limited to, antioxidants, astringents, perfumes, preservatives, emollients, pigments, dyes, humectants, propellants, and sunscreen agents, as well as other classes of materials whose presence can be pharmaceutically or otherwise desirable. Typical examples of optional additives for inclusion in the formulations of the disclosure are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), β-tocopherol, gamma-tocopherol, delta-tocopherol, epsilon-tocopherol, zeta-tocopherol, Z GAMMA-tocopherol, eta-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that can be obtained commercially under the Carbopol trademark. Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (Vitamin C), a-tocopherol (Vitamin E), beta-tocopherol, gamma-tocopherol, delta-tocopherol, epsilon-tocopherol, zeta-tocopherol, zeta 2-tocopherol, eta-tocopherol, and retinol (Vitamin A), and/or pharmaceutically acceptable salts, esters, amides, or other derivatives thereof. In some embodiments the tocopherol compound is a-tocopherol. Additional agents include those that are capable of improving oxygen supply in skin tissue, as described, for example, in Gross, et al, WO 94/00098 and Gross, et al, WO 94/00109, both assigned to Lancaster Group AG (incorporated herein by reference). Sunscreens and UV absorbing compounds can also be included. Non-limiting examples of such sunscreens and UV absorbing compounds include aminobenzoic acid (PABA), avobenzone, cinoxate, dioxybenzone, homosalate, menthyl anthranilate, oxtocrylene, octyl methoxycmnamate, octyl salicylate, oxybenzone, padirnate O, phenylbenzirmdazole sulfonic acid, sulisobenzone, titanium dioxide, trolamine salicylate, zinc oxide, ensulizole, meradiraate, octinoxate, octisalate, and octocrylene. See, Title 21. Chapter 1. Sub-chapter D. Part 352. "Sunscreen drug products for over-the-counter human use" incorporated herein in its entirety.

Other embodiments can include a variety of non-carcinogenic, non-irritating healing materials that facilitate treatment with the formulations of the disclosure. Such healing materials can include nutrients, minerals, vitamins, electrolytes, enzymes, herbs, plant extracts, glandular or animal extracts, or safe therapeutic agents that can be added to the formulation to facilitate the healing of dermal disorders. The amounts of these various additives are those conventionally used in the cosmetics field, and range, for example, from about 0.01% to about 20% of the total weight of the topical formulation.

The formulations of the disclosure can also include conventional additives such as opacifiers, fragrance, colorant, stabilizers, surfactants, and the like. In certain embodiments, other agents can also be added, such as antimicrobial agents, to prevent spoilage upon storage, i.e., to inhibit growth of microbes such as yeasts and molds.

The formulations can also contain irritation-mitigating additives to minimize or eliminate the possibility of skin irritation or skin damage resulting from the chemical entity to be administered, or other components of the composition. Suitable irritation-mitigating additives include, for example: a-tocopherol; monoamine oxidase inhibitors, particularly phenyl alcohols such as 2-phenyl-1-ethanol; glycerin; salicylates; ascorbates; ionophores such as monensin; amphophilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt. %, more typically not more than about 5 wt. %, of the formulation.

Further suitable pharmacologically active agents that can be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; anti-inflammatory agents; local anesthetics and analgesics; corticosteroids; retinoids; vitamins; hormones; and antimetabolites. Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycmnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil.

A cream, lotion, gel, ointment, paste or the like can be spread on the affected surface and gently rubbed in. A solution can be applied in the same way, but more typically will be applied with a dropper, swab, or the like, and carefully applied to the affected areas.

The pharmaceutical compositions of the disclosure comprise one or more active ingredients, e.g. therapeutic agents, in admixture with one or more pharmaceutically-acceptable diluents or carriers and, optionally, one or more other compounds, drugs, ingredients and/or materials. Regardless of the route of administration selected, the agents/compounds of the present disclosure are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable diluents or carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the disclosure must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the disclosure may, optionally, contain additional ingredients and/or materials commonly used in pharmaceutical and/or over-the-counter compositions. These ingredients and materials are well known in the art and non-limiting examples include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

In some embodiments, the compositions disclosed herein may be combined with an active drug substance that is potentially irritating to a subject's skin, such as alpha hydroxy acids, retinoic acids, benzoyl peroxide, calcipotriene, calcineurin inhibitors, sunscreens, sunblocks, bleaching agents, depilitories, antiperspirants, or combinations thereof. In some embodiments, the active drug substance may be anti-rosacea agents such as metronidazole, precipitated sulfur, sodium sulfacetamide, or azelaic acid; antibacterial agents (antibiotics) such as clindamycin phosphate, erythromycin, or antibiotics from the tetracycline family; antimycobacterial agents such as dapsone; other antiacne agents such as retinoids, or benzoyl peroxide; antiparasitic agents such as metronidazole, permethrin, crotamiton, thiabendazole, ivermectin or pyrethroids; antifungal agents such as compounds of the imidazole family such as miconazole, clotrimazole, econazole, ketoconazole, or salts thereof, polyene compounds such as amphotericin B, compounds of the allylamine family such as terbinafine.

In some embodiments, the compositions disclosed herein may comprise additional anti-inflammatory agents, such as steroidal anti-inflammatory agents including hydrocortisone triamcinolone, fluocinonide, betamethasone valerate or clobetasol propionate, or non-steroidal anti-inflammatory agents such as ibuprofen and salts thereof, naproxen and salts thereof, or acetaminophen. In some embodiments, the compositions disclosed herein may comprise anesthetic agents such as the "amide" and "ester" anesthetics such as lidocaine, prilocaine, tetracaine, hydrochloride and derivatives thereof. In some embodiments, the compositions disclosed herein may comprise antipruriginous agents such as thenaldine, trimeprazine, or pramoxine. In some embodiments, the compositions disclosed herein may comprise antiviral agents such as acyclovir. In some embodiments, the compositions disclosed herein may comprise keratolytic agents such as alpha- and beta-hydroxy acids such as glycolic acid or salicylic acid, or urea. In some embodiments, the compositions disclosed herein may comprise anti-free radical agents (antioxidants) such as Vitamin E (alpha tocopherol) and its derivatives, Vitamin C (ascorbic acid), Vitamin A (retinol) and its derivatives, and superoxide dismutases. In some embodiments, the compositions disclosed herein may comprise antiseborrheic agents such as zinc pyrithione and selenium sulfide. In some embodiments, the compositions disclosed herein may comprise antihistamines such as cyproheptadine or hydroxyzine. In some embodiments, the compositions disclosed herein may comprise antipsoriatic agents such as calcipotriene, anthralines, coal tar. In some embodiments, the compositions disclosed herein may comprise immune modulating agents such as imiquimod. In some embodiments, the compositions disclosed herein may comprise calcineurin inhibitors pimecrolimus and tacrolimus.

Methods for Healing a Wound and/or Treating an Inflammatory Skin Condition

Also disclosed herein are compositions and methods for healing a wound and/or treating an inflammatory skin condition. In some embodiments, the methods described herein promote wound closure and healing. In some embodiments, the compositions and methods described herein prevent scar formation during healing. In some embodiments, the compositions and methods disclosed herein are effective for treatment of inflammatory skin conditions. In some embodiments, the compositions and methods disclosed herein are effective to improve rosacea as measured by the standard grading system for rosacea, which grades the condition from absent, mild, moderate, or severe (grades 0-3, respectively). In some embodiments, the compositions and methods disclosed herein are effective to improve the clinical grade of rosacea by at least on grade (e.g., grade 1 to grade 0), at least two grades (e.g., grade 2 to grade 0), or at least three grades (e.g., grade 3 to grade 0).

In some embodiments, the compositions disclosed herein are effective to treat one or more types of inflammatory skin conditions such as rosacea, including erythematotelangiectatic rosacea, papulopustular rosacea, phymatous rosacea, ocular rosacea or combinations thereof. In some embodiments, the compositions disclosed herein are effective to treat the symptoms associated with rosacea, including, for example, papules, pustules, phymas (skin thickening), telangiectasias or erythema associated with rosacea, other skin erythemas, telangiectasias, purpura or the like, and other manifestations associated therewith.

In some embodiments, the compositions disclosed herein are effective to treat other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier. In some embodiments, the compositions disclosed herein are effective to treat disorders characterized by rough, dry, cracked or fissured skin, disorders characterized by hyperkeratotic skin such as keratodermas and ichthyosisis and ichthyosiform dermatoses. In some embodiments, the compositions disclosed herein are effective to treat disorders of hair follicles and sebaceous glands, such as acne, perioral dermatitis, and pseudofolliculitis barbae. In some embodiments, the compositions disclosed herein are effective to treat disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"). In some embodiments, the compositions disclosed herein are effective to treat other inflammatory dermatoses, reactions and conditions of the skin, including, but not limited to, psoriasis, drug eruptions, erythema multiforme, erythema nodosum, and granuloma annulare. In some embodiments, the compositions disclosed herein are effective to treat diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma. In some embodiments, the compositions disclosed herein are effective to treat infection, inflammatory dermatoses or inflammation due to any cause.

In some embodiments, the compositions disclosed herein are effective to treat rosacea, eczema, dermatitis, atopic dermatitis, psoriasis, steroid-responsive dermatoses, pruritis, or xerosis. In some embodiments, the compositions disclosed herein may be used to treat dry, irritated, erythematous or pruriginous skin in subjects with no underlying skin disease, such as, for example, after physical skin trauma or mechanical skin trauma such as shaving (e.g., as a post-shave healer) or tweezing, after bathing, showering, sweating; or after exposure to environmental factors, such as sun, wind, cold temperature, low humidity, hot and humid conditions, radiation, air pollution, smoke or cigarette smoke; or treat said skin irritation or erythema that is as a result of exposure to a topical irritant such as a chemical agent, insect sting or bite, plant exposure, or application of a topically applied drug product, medicament or topical product, such as a fragrance, insect repellant, exfoliant, skin peeling agent, shaving or depilatory preparation, skin or hair cleanser, soap, detergent or conditioner, hair treatment or colorant, antiperspirant, deodorant, sunscreen, tanning agent, moisturizer, astringent, toner, moisturizer, serum, mask, facial or body cosmetic, ointment, cream, lotion, gel, foam, solution, shake, or powder.

Another aspect of the disclosure is directed to a method for healing a wound and/or treating an inflammatory skin condition in a subject comprises administering to the subject in need thereof a wound healing composition and/or compositions for treating an inflammatory skin condition comprising: (a) a copper-containing peptide; (b) an antioxidant; and (c) a cyclic oligosaccharide-based polymer, wherein the copper-containing peptide and the antioxidant form a complex.

In some embodiments, the copper-containing peptide comprises glycyl-L-histidyl-L-lysine copper (GEM-Cu) peptide. In some embodiments, the composition comprises, by weight of the total composition, 0.1%-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) of copper-containing peptide. In some embodiments, the composition comprises, by weight of the total composition, 0.1%-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) GHK-Cu peptide.

In some embodiments, the antioxidant comprises L-carnosine, D-carnosine, acetyl-carnosine, anserine, alanine, L-histidine, D-histidine, a derivative thereof, or a combination thereof. In some embodiments, the antioxidant comprises carnosine. In some embodiments, the antioxidant comprises anserine. In some embodiments, the antioxidant comprises L-carnosine. In some embodiments, the composition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) antioxidant. In some embodiments, the composition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) carnosine. In some embodiments, the composition comprises, by weight of the total composition, 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) L-carnosine.

In some embodiments, the composition comprises GHK-Cu peptide, carnosine, and cyclodextrin. In some embodiments, the composition comprises GHK-Cu peptide, L-carnosine, and gamma cyclodextrin.

In some embodiments, the cyclic oligosaccharide-based polymer comprises an alpha cyclodextrin, beta cyclodextrin, a gamma cyclodextrin, a 2-hydroxypropyl-β-cyclodextrin, a β-cyclodextrin sulfobutylether, hydroxyethyl-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-1-β-cyclodextrin, glocosyl-β-cyclodextrin, maltosyl-β-cyclodextrin or any derivative thereof, and any combination thereof. In some embodiments, the cyclic oligosaccharide-based polymer is non-crosslinked. In some embodiments, the cyclic oligosaccharide-based polymer is crosslinked. In some embodiments, the cyclic oligosaccharide-based polymer is an alkylated derivative. In some embodiments, the composition comprises, by weight of the total composition, 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclic oligosaccharide-based polymer. In some embodiments, the wound healing composition and/or compositions for treating an inflammatory skin condition comprises, by weight of the total composition, 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclodextrin or an alkylated derivative thereof. In some embodiments, the wound healing composition and/or compositions for treating an inflammatory skin condition comprises, by weight of the total composition, 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) gamma cyclodextrin or an alkylated derivative thereof.

In some embodiments, the cyclic oligosaccharide-based polymer comprises gamma cyclodextrin. In some embodiments, the gamma cyclodextrin comprises non-crosslinked gamma cyclodextrin. In some embodiments, the gamma cyclodextrin comprises crosslinked gamma cyclodextrin.

In some embodiments, the alpha cyclodextrin has the following chemical formula:

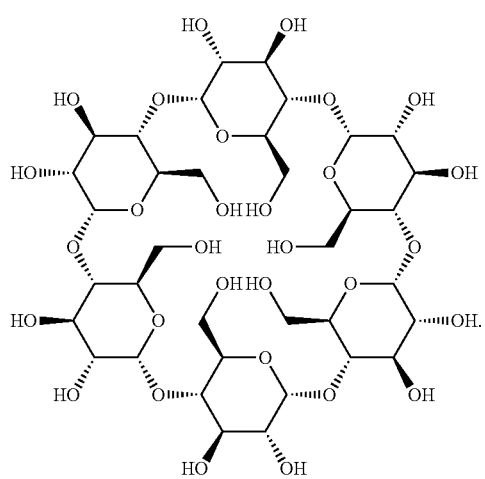 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]1[C@H](O)[C@H]2O)O[C@@H]7CO)O[C@@H]6CO)O[C@@H]5CO)O[C@@H]4CO)O[C@@H]3CO]

In some embodiments, the beta cyclodextrin has the following chemical formula:

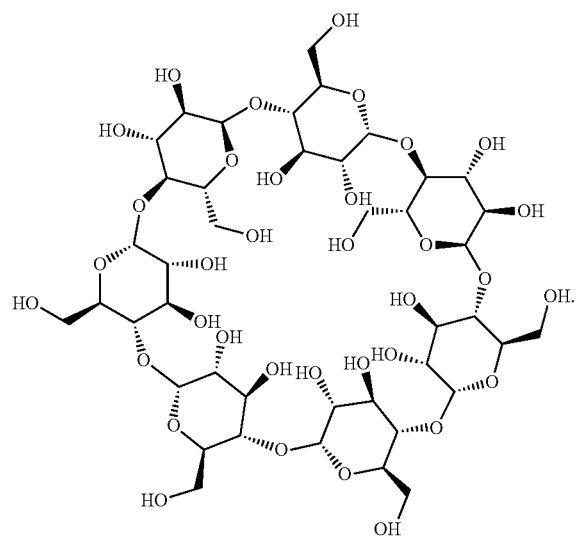 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]1[C@H](O)[C@H]2O)O[C@@H]8CO)O[C@@H]7CO)O[C@@H]6CO)O[C@@H]5CO)O[C@@H]4CO)O[C@@H]3CO]

In some embodiments, the gamma cyclodextrin has the following chemical formula:

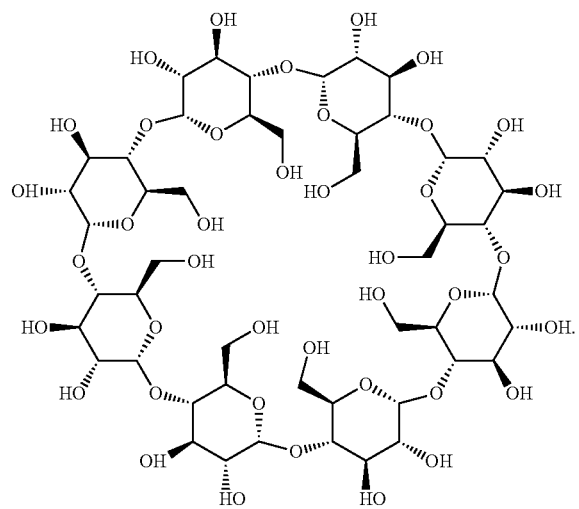 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]9[C@H](O)[C@@H](O)[C@@H](O[C@H]1[C@H](O)[C@H]2O)O[C@@H]9CO)O[C@@H]8CO)O[C@@H]7CO)O[C@@H]6CO)O[C@@H]5CO)O[C@@H]4CO)O[C@@H]3CO]

In some embodiments, the complex formed by the copper-containing peptide and the antioxidant is purple in color, while the copper-containing peptide is blue in color. In some embodiments, the complex formed by GHK-Cu peptide and carnosine is purple in color. In some embodiments, the complex formed by GHK-Cu peptide and L-carnosine is purple in color.

In some embodiments, the wound healing composition and/or composition for treating an inflammatory skin condition has a pH between 5.5 and 7.3 (e.g., pH 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3 or any value therebetween). In some embodiments, the composition has a pH between band 7 (e.g., pH 6, 6.1, 6.2, 6.3, 6.4, 6.5, 6.6, 6.7, 6.8, 6.9, 7, or any value therebetween).

In some embodiments, the copper-containing peptide is entrapped by the cyclic oligosaccharide-based polymer. In some embodiments, the GHK-Cu peptide is entrapped by cyclodextrin. In some embodiments, the GHK-Cu peptide is entrapped by gamma cyclodextrin. In some embodiments, the complex formed by the copper-containing peptide and the antioxidant is entrapped by the cyclic oligosaccharide-based polymer. In some embodiments, the complex formed by GHK-Cu peptide and carnosine is entrapped by cyclodextrin. In some embodiments, the complex formed by GHK-Cu peptide and L-carnosine is entrapped by gamma cyclodextrin.

In some embodiments, the wound healing composition and/or composition for treating an inflammatory skin condition comprises by weight of the total composition: (a) 0.1%-2% copper-containing peptide (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween); (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) antioxidant; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclic oligosaccharide-based polymer.

In some embodiments, the wound healing composition and/or composition for treating an inflammatory skin condition comprises by weight of the total composition: (a) 0.1%-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) copper-containing peptide; (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) carnosine; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) cyclodextrin.

In some embodiments, the wound healing composition and/or composition for treating an inflammatory skin condition comprises by weight of the total composition: (a) 0.1%-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2%, or any value therebetween) GHK-Cu peptide; (b) 0.5%-10% (0.5, 0.7, 1, 1.5, 2, 2.5, 3, 3.5, 4, 4.5, 5, 5.5, 6, 6.5, 7, 7.5, 8, 8.5, 9, 9.5, 10% or any value therebetween) L-carnosine; and (c) 0.1%-20% (0.1, 0.5, 0.7, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20% or any value therebetween) gamma cyclodextrin.

In some embodiments, the wound healing composition and/or composition for treating an inflammatory skin condition further comprises at least one pharmaceutically acceptable carrier or excipient.

In some embodiments, the wound healing composition and/or composition for treating an inflammatory skin condition further comprises at least one of: a pH buffer; a humectant; a nonionic surfactant; and a preservative.

In some embodiments, the wound healing composition and/or composition for treating an inflammatory skin condition comprises 0.05%-3% (e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3%, or any value therebetween) pH buffer. In some embodiments, the wound healing composition and/or compositions for treating an inflammatory skin condition comprises 3%-30% (e.g., 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30%, or any value therebetween) humectant. In some embodiments, the wound healing composition and/or compositions for treating an inflammatory skin condition comprises 5%-15% (5, 5.5, 6, 6.5, 7, 7.5, 8, 8.5, 9, 9.5, 10, 10.5, 11, 11.5, 12, 12.5, 13, 13.5, 14, 14.5, 15%, or any value therebetween) nonionic surfactant. In some embodiments, the wound healing composition and/or compositions for treating an inflammatory skin condition comprises 0.05%-1.5% (e.g., 0.05, 0.1, 0.2, 0.3, 0.4, 0.5, 0.6, 0.7, 0.8, 0.9, 1, 1.1, 1.2, 1.3, 1.4, 1.5, or any value therebetween) preservative.

In some embodiments, the pH buffer comprises at least one of citric acid, magnesium citrate, magnesium sulfate, sodium citrate or sodium sulfate. In some embodiments, the pH buffer comprises citric acid.

In some embodiments, the humectant comprises at least one of an amino acid, aloe vera extract, a fatty acid, hyaluronic acid (HA), collagen, silicone, a disaccharide (e.g., sucrose or trehalose), maltitol, erythrol, sorbitol, glycerin, propanediol, propylene glycol, glycerin or any other glycol/diol. In some embodiments, the humectant comprises glycerin and/or HA. In some embodiments, HA is swapped for any other heavy molecular weight polymer such as collagen or a derivative. In some embodiments, collagen is interchangeable with HA or can be combined with HA, e.g., 0.6% HA combined with 0.5% collagen. In some embodiments, the composition comprises 0.2-5% of HA, 0.2-5% of collagen or derivatives thereof, or 0.2-5% of HA and collagen or a derivative thereof combined. In some embodiments, the composition comprises 3-30% (e.g., 3, 4, 5, 6, 7, 8, 9, 10, 11, 12, 13, 14, 15, 16, 17, 18, 19, 20, 21, 22, 23, 24, 25, 26, 27, 28, 29, 30% or any number therebetween) of propanediol, propylene glycol, glycerin or any other glycol/diol, or a combination thereof.

In some embodiments, the nonionic surfactant comprises at least one of tearyl alcohol, cetearyl alcohol, or a combination of both. In some embodiments, the nonionic surfactant comprises tearyl alcohol. In some embodiments, the nonionic surfactant comprises cetearyl alcohol. In some embodiments, the composition comprises 3-30% of a nonionic surfactant.

In some embodiments, the preservative comprises at least one of sodium benzoate, paraben, benzyl alcohol, sorbic acid, triclosan, phenoxyisopropanol, diazolidinyl urea, bronopol, Alkyl (C12-22) trimethyl ammonium bromide, Alkyl (C12-22) trimethyl ammonium chloride, Benzalkonium chloride, Benzalkonium bromide, Benzalkonium saccharinate, or phenoxyethanol. In some embodiments, the preservative comprises phenoxyethanol or ethylhexylglycerin or both, optionally at 0.5%-1.5% of the composition. In some embodiments, the phenoxyethanol or ethylhexylglycerin can be swapped for parabens or other aromatic alcohols such as benzyl alcohol, optionally at 0.5%-1.5% of the composition.

In some embodiments, the wound healing composition and/or composition for treating an inflammatory skin condition further comprises at least one of the following constituents: sunflower oil, Tegomuls 90 S, cetyl alcohol, cetyl palmitate, Polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil or distilled water.

In some embodiments, the wound healing composition and/or composition for treating an inflammatory skin condition further comprises at least one constituent selected from the group consisting of an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, and an antipruritic agent.

In some embodiments, the composition is lyophilized. In some embodiments, the composition is spray dried to form a sterile powder. In some embodiments, the composition is freeze dried onto a wound dressing patch.

In some embodiments, the wound healing composition and/or composition for treating an inflammatory skin condition is a patch, a cream, an ointment, a powder, an aerosol spray, or a hydrogel. In some embodiments, the wound healing composition and/or compositions for treating an inflammatory skin condition is impregnated into a dressing.

In some embodiments, the wound healing composition and/or composition for treating an inflammatory skin condition is administered topically.

In some embodiments, the wound healing composition and/or composition for treating an inflammatory skin condition is administered every hour, every two hours, every three hours, every six hours, every twelve hours, every day, every two days, every three days, every five days, every seven days, every ten days, or every fourteen days.

In some embodiments, the wound is a bed sore, an incision, an excision, a laceration, an abrasion, a puncture or a penetrating wound, a surgical wound, a contusion, a hematoma, a crushing injury, a burn ulcer, an acne scar or a shingles rash. In some embodiments, the wound is a shingles rash.

In some embodiments, the composition is used for skin repair. In some embodiments, the composition is used to repair a skin wound caused by a dermatological treatment (e.g., a chemical peel, a laser treatment or micro needling).

In some embodiments, the method comprises administering a sunscreen in combination with the wound healing composition and/or composition for treating an inflammatory skin condition, wherein the composition and the sunscreen can be administered simultaneous or sequentially.

The terminology used herein is for the purpose of describing particular embodiments only and is not intended to be limiting. As used in the specification and the appended claims, the singular forms "a," "an," and "the" include plural referents unless the context clearly dictates otherwise.

The following examples are provided to further illustrate the methods of the present invention. These examples are illustrative only and are not intended to limit the scope of the invention in any way.

EXAMPLES

Example 1: Composition for Use in Treatment of a Wound and/or Treatment of an Inflammatory Skin Condition A wound healing composition and/or composition for treatment of an inflammatory skin condition comprising the following ingredients was prepared: 0.2% GHK-Cu peptide, 2% Carnosine, 1% Gamma-Cyclodextrin, 0.51% Citric acid, 3% Glycerin, 10% Propanediol, 0.7% Phenoxyethanol, 0.1% Ethylhexylglycerin, 0.8% HA. The composition has a distinctive purple color at pH between 6 and 7 (FIG. 1); in contrast, the GHK-Cu peptide solution is blue in color (FIG. 2).

An additional wound healing composition and/or composition for treatment of an inflammatory skin condition comprising the following ingredients was also prepared: 0.4% GHK peptide, 4% Carnosine, 1% Gamma-Cyclodextrin, 1% Citric acid, 2% Glycerin, 10% Propanediol, 0.7% Phenoxyethanol, 0.1% ethylhexylglycerin, 1% HA, Q.S $H_2O$. An further wound healing composition and/or composition for treatment of an inflammatory skin condition comprising the following ingredients was also prepared: 0.2% GHK peptide, 2% Carnosine, 1% Gamma-Cyclodextrin, 0.5% Citric acid, 2% Glycerin, 10% Propanediol, 0.7% Phenoxyethanol, 0.1% ethylhexylglycerin, 1% HA, Q.S $H_2O$.

Example 2: Gene Expression Analysis

A stock of Carnosine at 4% (meaning 177 mM) was made from a keratinocyte complete media and Fibroblast complete media at 1:1 ratio. The keratinocyte complete media is composed of Dermal Cell Basal Medium (ATCC, catalog #PCS-200-030) mixed with Keratinocyte Growth Kit (ATCC, catalog #PCS-200-040) as specified by ATCC. The Fibroblast complete media is composed of Eagle's Minimum Essential Medium (EMEM) (ATCC, catalog #30-2003) mixed with 10% of decomplimented fetal bovine serum (Cytiva, catalog #SH30088.03) as specified by ATCC.

Primary adult normal Human Epidermal Keratinocytes (HEKa) (ATCC, catalog #PCS-200-011) were cultivated and expanded as a monoculture in complete Keratinocyte media; epidermal meaning from skin. Adult normal human skin fibroblasts (ATCC, catalog #CRL-2091) were cultivated and expanded as a monoculture in complete Fibroblast media.

When the experiments were set up, at that time only, both cells were cultivated together at a ratio of 1:1, using a made-up media of complete Keratinocyte media and complete Fibroblast media at a ratio 1:1.

The experiments were used to identify biomarkers associated with wound healing on the co-culture of primary adult normal Epidermal Keratinocytes (HEKa) (ATCC, catalog #PCS-200-011) with adult normal skin fibroblasts (ATCC, catalog #CRL-2091). Both types of cells were plated at the same time and allowed to attach to the plate. After 24h, multiple co-cultures of cells were dosed with different concentrations of Carnosine, each condition in six replicates). After 24 of dosing, the media was discarded and fresh keratinocyte media/fibroblast media (1:1 ratio) without carnosine, was added to each co-culture condition. After an additional 24 h, the cells were lysed using lysis buffer (RLA with beta-mercaptoethanol) from a kit of total RNA extraction (SV Total RNA Isolation System) as specified by the vendor (Promega). Each condition, each replicate was extracted as a unique RNA sample.

After total RNA extraction, RNA was quantified and checked for quality by measuring the Optical Density of each individual RNA sample. A reverse transcription was performed on each individual RNA sample at 300ng of total RNA using the SuperScript™ IV VILO™ Master Mix from vendor ThermoFisher Scientific following manufacturer instructions to produce a cDNA equivalent to each RNA sample in a machine used as a thermocycler.

After reverse transcription, each sample was diluted 1:1 with molecular biology grade water. After dilution of the cDNA samples, real-time PCR was performed on each cDNA sample (15ng) set as multiplex, meaning two Taqmans were used simultaneously for each sample using a real-time PCR machine; one Taqman was the Eukaryotic 18S rRNA Endogenous Control the other Taqman was the target gene. The real-time PCR data is run as comparative Ct (delta delta Ct).

There was a new real-time PCR for each couple Eukaryotic 18S rRNA Endogenous Control the other Taqman was the target gene versus target gene Taqman. All target genes Taqmans were for human genes. Target genes were selected for genes know to play a role in wound healing. The different couples were as follows:

Eukaryotic 18S rRNA Endogenous Control Taqman (VIC™/MGB probe, primer limited, ThermoFisher Scientific, catalog #4319413E) and h COL1A2 (ThermoFisher Scientific, Assay ID #Hs01028956_m1)

Eukaryotic 18S rRNA Endogenous Control Taqman (VIC™/MGB probe, primer limited, ThermoFisher Scientific, catalog #4319413E) and h EGF-1 (ThermoFisher Scientific, Assay ID #Hs01099990_m1)

Eukaryotic 18S rRNA Endogenous Control Taqman (VIC™/MGB probe, primer limited, ThermoFisher Scientific, catalog #4319413E) and h MMP-1 (ThermoFisher Scientific, Assay ID #Hs00899658_m1)

Eukaryotic 18S rRNA Endogenous Control Taqman (VIC™/MGB probe, primer limited, ThermoFisher Scientific, catalog #4319413E) and h ELN (ThermoFisher Scientific, Assay ID #Hs00355783_m1)

Eukaryotic 18S rRNA Endogenous Control Taqman (VIC™/MGB probe, primer limited, ThermoFisher Scientific, catalog #4319413E) and h FLG (ThermoFisher Scientific, Assay ID #Hs00856927_g1)

Eukaryotic 18S rRNA Endogenous Control Taqman (VIC™/MGB probe, primer limited, ThermoFisher Scientific, catalog #4319413E) and h IGF-1 (ThermoFisher Scientific, Assay ID #Hs01547656_m1)

Eukaryotic 18S rRNA Endogenous Control Taqman (VIC™/MGB probe, primer limited, ThermoFisher Scientific, catalog #4319413E) and h ACTA2 (ThermoFisher Scientific, Assay ID #Hs00426835_g1)

Eukaryotic 18S rRNA Endogenous Control Taqman (VIC™/MGB probe, primer limited, ThermoFisher Scientific, catalog #4319413E) and h HAVCR1 (ThermoFisher Scientific, Assay ID #Hs00930379_g1)

Eukaryotic 18S rRNA Endogenous Control Taqman (VIC™/MGB probe, primer limited, ThermoFisher Scientific, catalog #4319413E) and h IFN-g (ThermoFisher Scientific, Assay ID #Hs00989291_m1)

Eukaryotic 18S rRNA Endogenous Control Taqman (VIC™/MGB probe, primer limited, ThermoFisher Scientific, catalog #4319413E) and h ANG-2 (ThermoFisher Scientific, Assay ID #Hs00169867_m1)

Real-time PCR was analyzed as comparative Ct (delta delta Ct) using the Eukaryotic 18S rRNA Endogenous Control Taqman values as endogenous control, using Excel (Microsoft). t TEST (sample compared to control) was performed for the obtained data, with p value equal of less than 0.05 being considered as specific.

The changes in gene expression observed after treatment are shown in FIG. 3.

Example 3: Human Testing for Skin Wound and Skin Inflammatory Conditions

Compositions as disclosed herein were applied to human subjects to test for improvement in wound healing and inflammatory skin conditions. Two formulas were tested. For treatment of scars on the skin of breast and leg, the following formula was applied topically every 12 hours: 0.4% GHK peptide, 4% Carnosine, 1% Gamma-Cyclodextrin, 1% Citric acid, 2% Glycerin, 10% Propanediol, 0.7% Phenoxyethanol, 0.1% ethylhexylglycerin, 1% HA, Q.S H$_2$O. For treatment of eczema and head wound, the following formula was applied topically every 12 hours: 0.2% GHK peptide, 2% Carnosine, 1% Gamma-Cyclodextrin, 0.5% Citric acid, 2% Glycerin, 10% Propanediol, 0.7% Phenoxyethanol, 0.1% ethylhexylglycerin, 1% HA, Q.S H$_2$O.

Figure 4:
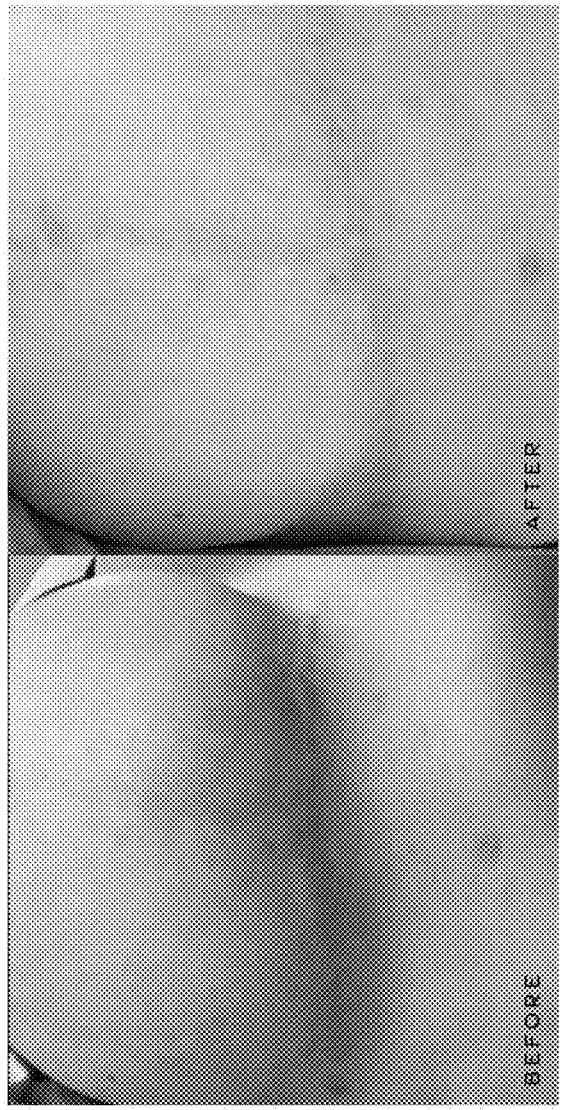
FIG. 4 shows the results of treatment of scar tissue on the breast of a human subject before and after application of one embodiment of the composition as disclosed herein.
Figure 5:
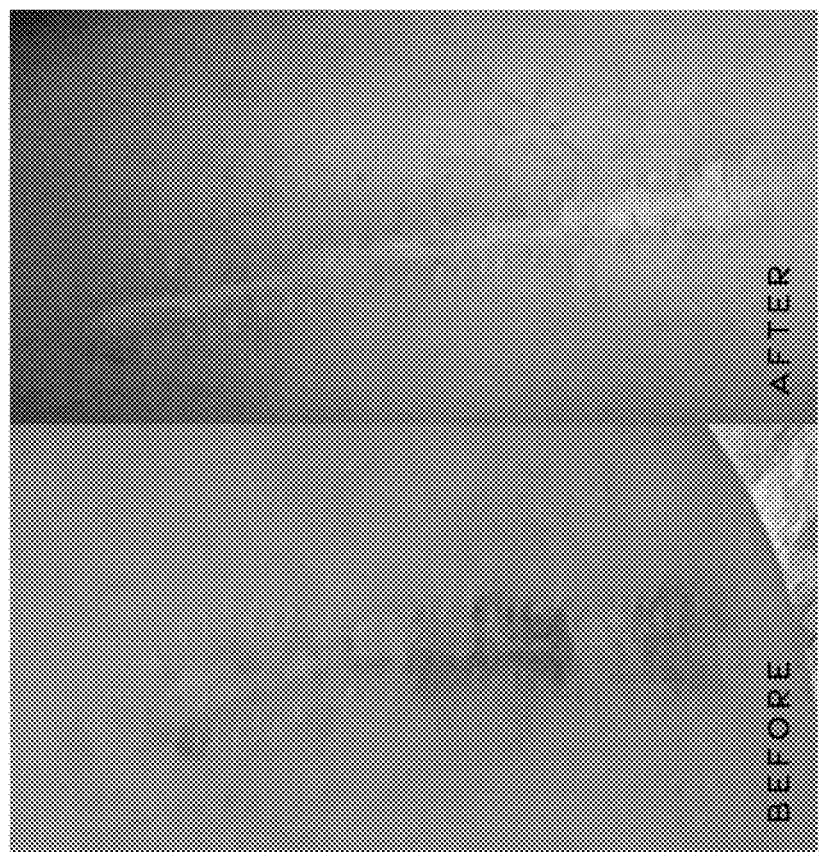
FIG. 5 shows the results of treatment of scar tissue on the leg of a human subject before and after application of one embodiment of the composition as disclosed herein.

Breast scars (thirteen years old) were treated as described above for 30 days. The images of FIG. 4 show a surprising improvement in scar tissue after the 30 day treatment. (Compare scar before treatment, FIG. 4, left panel, with scar tissue after 30 day treatment, FIG. 4, right panel). Leg scar tissue (fifteen years old) was treated as described above for 35 days. The images of FIG. 5 show a surprising improvement in the appearance of scar tissue on the leg after the 35 day treatment. (Compare scar tissue before treatment, FIG. 5, left panel, with scar tissue after 35 day treatment, FIG. 5, right panel).

Figure 6:
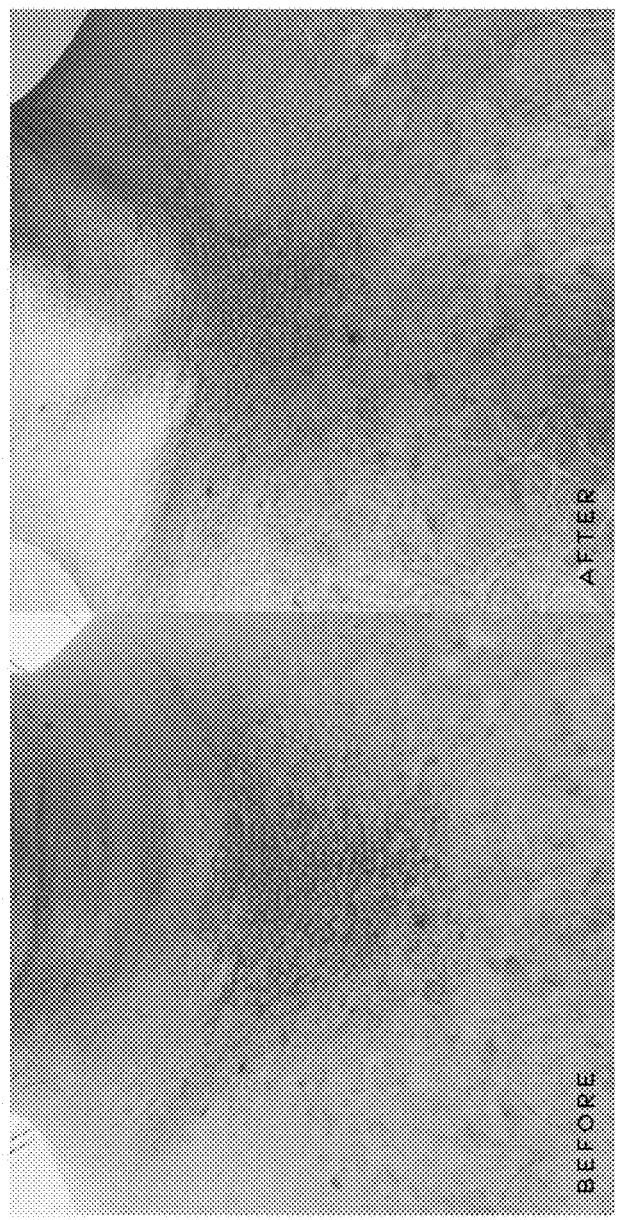
FIG. 6 shows the results of treatment of eczema on the chest of a human subject before and after application of one embodiment of the composition as disclosed herein.
Figure 7:
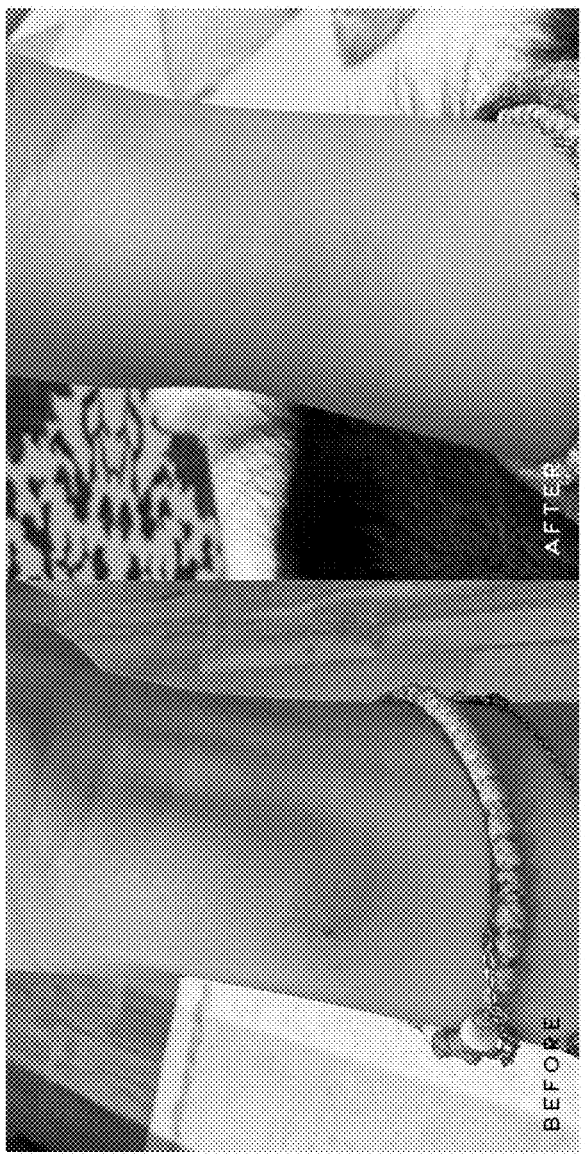
FIG. 7 shows the results of treatment of eczema on the arm of a human subject before and after application of one embodiment of the composition as disclosed herein.

Eczema on the chest was treated as described above for 13 days. The images of FIG. 6 show a surprising improvement in eczema, including a reduction in red appearance of the skin after the 13 day treatment. (Compare eczema before treatment, FIG. 6, left panel, with eczema after 13 day treatment, FIG. 6, right panel). Eczema on the wrist was treated as described above for 48 hours. The images of FIG. 7 show a surprising improvement in eczema, including a reduction in red appearance of the skin after the 48 hour treatment. (Compare eczema before treatment, FIG. 7, left panel, with FIG. 7, right panel)

Figure 8:
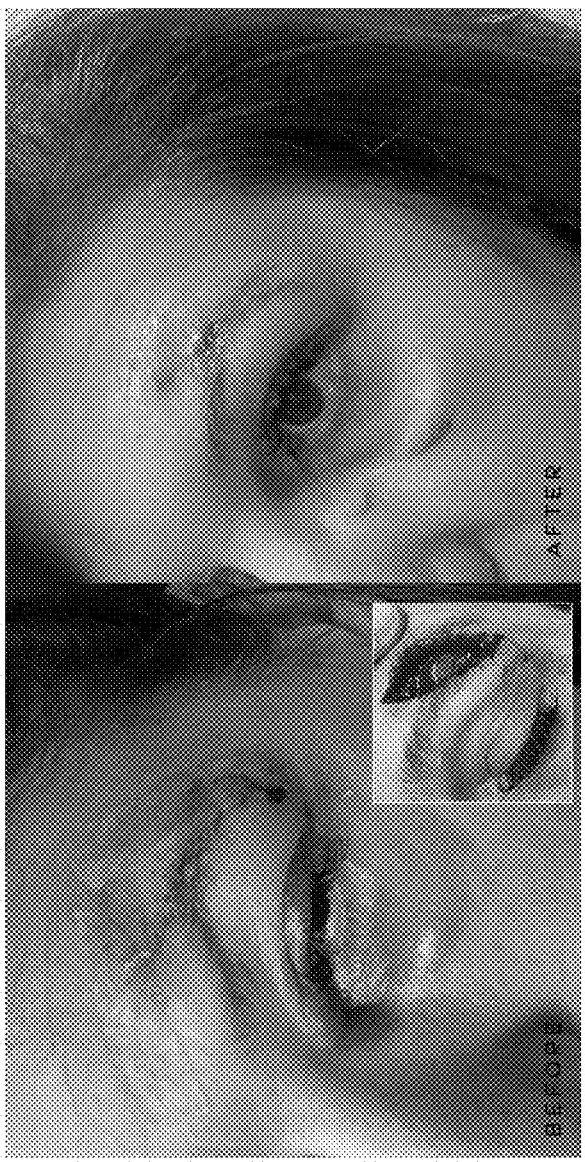
FIG. 8 shows the results of treatment of a wound on the forehead/eyebrow of a human subject before and after application of one embodiment of the composition as disclosed herein.

An eyebrow wound was treated as described above for 6 days. The images of FIG. 8 show a surprising improvement in inflammation associated with the wound and healing of the wound after the 6 day treatment. (Compare wound before treatment FIG. 8, left panel, with wound after 6 days of treatment, FIG. 8, right panel).

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes can be made by those skilled in the art without departing from the spirit of this disclosure. Those skilled in the art will appreciate that the inventive principles can be practiced in other than the described embodiments, which are presented for purposes of illustration and not limitation.

Various Embodiments

Embodiment 1. A composition for use in healing a wound and/or treating an inflammatory skin condition comprising:
 (a) a copper-containing peptide;
 (b) an antioxidant; and
 (c) a cyclic oligosaccharide-based polymer,
wherein the copper-containing peptide and the antioxidant form a complex.

Embodiment 2. The composition of any preceding Embodiment, wherein the copper-containing peptide comprises glycyl-L-histidyl-L-lysine copper (GHK-Cu) peptide.

Embodiment 3. The composition of any preceding Embodiment, wherein the antioxidant comprises L-carnosine, D-carnosine, acetyl-carnosine, anserine, alanine, L-histidine, D-histidine, a derivative thereof, or a combination thereof.

Embodiment 4. The composition of any preceding Embodiment, wherein the antioxidant comprises L-carnosine.

Embodiment 5. The composition of any preceding Embodiment, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

Embodiment 6. The composition of any preceding Embodiment, wherein the cyclic oligosaccharide-based polymer comprises gamma cyclodextrin, optionally a non-crosslinked gamma cyclodextrin.

Embodiment 7. The composition of any preceding Embodiment, comprising GHK-Cu peptide, carnosine, and cyclodextrin.

Embodiment 8. The composition of any preceding Embodiment, comprising GHK-Cu peptide, L-carnosine, and gamma cyclodextrin.

Embodiment 9. The composition of any preceding Embodiment, wherein the complex formed by the copper-containing peptide and the antioxidant is purple in color.

Embodiment 10. The composition of any preceding Embodiment, wherein the composition has a pH between 5.5 and 7.3.

Embodiment 11. The composition of any preceding Embodiment, wherein the complex formed by the copper-containing peptide and the antioxidant is entrapped by the cyclic oligosaccharide-based polymer.

Embodiment 12. The composition of any preceding Embodiment, comprising by weight of the total composition: (a) 0.1%-2% copper-containing peptide; (b) 0.5%-10% antioxidant; and (c) 0.1%-20% cyclic oligosaccharide-based polymer.

Embodiment 13. The composition of any preceding Embodiment, comprising by weight of the total composition: (a) 0.1%-2% copper-containing peptide; (b) 0.5%-10% carnosine; and (c) 0.1%-20% cyclodextrin.

Embodiment 14. The composition of any preceding Embodiment, comprising by weight of the total composition: (a) 0.1%-2% GHK-Cu peptide; (b) 0.5%-10% L-carnosine; and (c) 0.1%-20% gamma cyclodextrin.

Embodiment 15. The composition of any preceding Embodiment, further comprising at least one pharmaceutically acceptable carrier or excipient.

Embodiment 16. The composition of any preceding Embodiment, wherein the composition is a patch, a cream, an ointment, a powder, an aerosol spray, or a hydrogel.

Embodiment 17. A method for healing a wound and/or treating an inflammatory skin condition in a subject comprising administering to the subject in need thereof a therapeutically effective amount of a composition comprising:
(a) a copper-containing peptide;
(b) an antioxidant; and
(c) a cyclic oligosaccharide-based polymer, wherein the copper-containing peptide and the antioxidant form a complex.

Embodiment 18. The method of any preceding Embodiment, wherein the copper-containing peptide comprises glycyl-L-histidyl-L-lysine copper (GHK-Cu) peptide.

Embodiment 19. The method of any preceding Embodiment, wherein the antioxidant comprises L-carnosine, D-carnosine, acetyl-carnosine, anserine, alanine, L-histidine, D-histidine, a derivative thereof, or a combination thereof.

Embodiment 20. The method of any preceding Embodiment, wherein the antioxidant comprises L-carnosine.

Embodiment 21. The method of any preceding Embodiment, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

Embodiment 22. The method of any preceding Embodiment, wherein the cyclic oligosaccharide-based polymer comprises gamma cyclodextrin, optionally non-crosslinked gamma cyclodextrin.

Embodiment 23. The method of any preceding Embodiment, wherein the composition comprises GHK-Cu peptide, carnosine, and cyclodextrin.

Embodiment 24. The method of any preceding Embodiment, wherein the composition comprises GHK-Cu peptide, L-carnosine, and gamma cyclodextrin.

Embodiment 25. The method of any preceding Embodiment, wherein the complex formed by the copper-containing peptide and the antioxidant is purple in color.

Embodiment 26. The method of any preceding Embodiment, wherein the composition has a pH between 5.5 and 7.3.

Embodiment 27. The method of any preceding Embodiment, wherein the complex formed by the copper-containing peptide and the antioxidant is entrapped by the cyclic oligosaccharide-based polymer.

Embodiment 28. The method of any preceding Embodiment, wherein the composition comprises by weight of the total composition: (a) 0.1%-2% copper-containing peptide; (b) 0.5%-10% antioxidant; and (c) 0.1%-20% cyclic oligosaccharide-based polymer.

Embodiment 29. The method of any preceding Embodiment, wherein the composition comprises by weight of the total composition: (a) 0.1%-2% copper-containing peptide; (b) 0.5%-10% carnosine; and (c) 0.1%-20% cyclodextrin.

Embodiment 30. The method of any preceding Embodiment, wherein the composition comprises by weight of the total composition: (a) 0.1%-2% GHK-Cu peptide; (b) 0.5%-10% L-carnosine; and (c) 0.1%-20% gamma cyclodextrin.

Embodiment 31. The method of any preceding Embodiment, wherein the composition further comprises at least one pharmaceutically acceptable carrier or excipient.

Embodiment 32. The method of any preceding Embodiment, wherein the composition is a patch, a cream, an ointment, a powder, an aerosol spray, or a hydrogel.

Embodiment 33. The method of any preceding Embodiment, wherein the composition is administered topically.

Embodiment 34. The method of any preceding Embodiment, wherein the composition is administered every hour, every two hours, every three hours, every six hours, every twelve hours, every day, every two days, every three days, every five days, every seven days, every ten days, or every fourteen days.

Embodiment 35. The method of any preceding Embodiment, wherein the wound is a bed sore, an incision, an excision, a laceration, an abrasion, a puncture or a penetrating wound, a surgical wound, a contusion, a hematoma, a crushing injury, a burn ulcer, an acne scar or a shingles rash.

Embodiment 36. The method of any preceding Embodiment, wherein the wound healing composition repairs a skin wound.

Embodiment 37. The method of any preceding Embodiment, wherein the skin wound is caused by a dermatological treatment selected from a chemical peel, a laser treatment or micro needling.

Embodiment 38. The method of any preceding Embodiment, further comprising administering a sunscreen.

Embodiment 39. A composition for altering gene expression of a skin cell in a human subject comprising:
(a) a copper-containing peptide;

(b) an antioxidant; and (c) a cyclic oligosaccharide-based polymer, wherein the copper-containing peptide and the antioxidant form a complex; and wherein the composition is effective to increase the gene expression of one or more of the genes hCOL1A2, hEGF-1, hMMP-1, hELN, hFLG, and hIGF-1.

Embodiment 40. The composition of any preceding Embodiment, wherein the copper-containing peptide comprises glycyl-L-histidyl-L-lysine copper (GHK-Cu) peptide.

Embodiment 41. The composition of any preceding Embodiment, wherein the antioxidant comprises L-carnosine, D-carnosine, acetyl-carnosine, anserine, alanine, L-histidine, D-histidine, a derivative thereof, or a combination thereof.

Embodiment 42. The composition of any preceding Embodiment, wherein the antioxidant comprises L-carnosine.

Embodiment 43. The composition of any preceding Embodiment, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

Embodiment 44. The composition of any preceding Embodiment, wherein the cyclic oligosaccharide-based polymer comprises gamma cyclodextrin.

Embodiment 45. The composition of any preceding Embodiment, wherein the gamma cyclodextrin is a non-crosslinked gamma cyclodextrin.

Embodiment 46. The composition of any preceding Embodiment, comprising GHK-Cu peptide, carnosine, and cyclodextrin.

Embodiment 47. The composition of any preceding Embodiment, comprising GHK-Cu peptide, L-carnosine, and gamma cyclodextrin.

Embodiment 48. The composition of any preceding Embodiment, wherein the complex formed by the copper-containing peptide and the antioxidant is purple in color.

Embodiment 49. The composition of any preceding Embodiment, wherein the composition has a pH between 5.5 and 7.3.

Embodiment 50. The composition of any preceding Embodiment, wherein the complex formed by the copper-containing peptide and the antioxidant is entrapped by the cyclic oligosaccharide-based polymer.

Embodiment 51. The composition of any preceding Embodiment, comprising by weight of the total composition: (a) 0.1%-2% copper-containing peptide; (b) 0.5%-10% antioxidant; and (c) 0.1%-20% cyclic oligosaccharide-based polymer.

Embodiment 52. The composition of any preceding Embodiment, comprising by weight of the total composition: (a) 0.1%-2% copper-containing peptide; (b) 0.5%-10% carnosine; and (c) 0.1%-20% cyclodextrin.

Embodiment 53. The composition of any preceding Embodiment, comprising by weight of the total composition: (a) 0.1%-2% GHK-Cu peptide; (b) 0.5%-10% L-carnosine; and (c) 0.1%-20% gamma cyclodextrin.

Embodiment 54. The composition of any preceding Embodiment, further comprising at least one pharmaceutically acceptable carrier or excipient.

Embodiment 55. The composition of any preceding Embodiment, wherein the composition is delivered by a patch, a cream, an ointment, a powder, an aerosol spray, or a hydrogel.

Embodiment 56. The composition of any preceding Embodiment, wherein the composition is effective to treat a wound or inflammatory condition of the skin.

Embodiment 57. The composition of any preceding Embodiment, wherein the inflammatory condition of the skin is eczema, rosacea, or combination thereof.

Embodiment 58. A method for altering gene expression of a human skin cell in a human subject comprising the steps of contacting the human skin cell with a composition comprising:

(a) a copper-containing peptide;

(b) an antioxidant; and (c) a cyclic oligosaccharide-based polymer, wherein the copper-containing peptide and the antioxidant form a complex; and wherein the gene expression is one or more of the genes hCOL1A2, hEGF-1, hMMP-1, hELN, hFLG, and hIGF-1.

Embodiment 59. The method of any preceding Embodiment, wherein the copper-containing peptide comprises glycyl-L-histidyl-L-lysine copper (GHK-Cu) peptide.

Embodiment 60. The method of any preceding Embodiment, wherein the antioxidant comprises L-carnosine, D-carnosine, acetyl-carnosine, anserine, alanine, L-histidine, D-histidine, a derivative thereof, or a combination thereof.

Embodiment 61. The method of any preceding Embodiment, wherein the antioxidant comprises L-carnosine.

Embodiment 62. The method of any preceding Embodiment, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

Embodiment 63. The method of any preceding Embodiment, wherein the cyclic oligosaccharide-based polymer comprises gamma cyclodextrin.

Embodiment 64. The method of any preceding Embodiment, wherein the gamma cyclodextrin is a non-crosslinked gamma cyclodextrin.

Embodiment 65. The method of any preceding Embodiment, comprising GHK-Cu peptide, carnosine, and cyclodextrin.

Embodiment 66. The method of any preceding Embodiment, comprising GHK-Cu peptide, L-carnosine, and gamma cyclodextrin.

Embodiment 67. The method of any preceding Embodiment, wherein the complex formed by the copper-containing peptide and the antioxidant is purple in color.

Embodiment 68. The method of any preceding Embodiment, wherein the composition has a pH between 5.5 and 7.3.

Embodiment 69. The method of any preceding Embodiment, wherein the complex formed by the copper-containing peptide and the antioxidant is entrapped by the cyclic oligosaccharide-based polymer.

Embodiment 70. The method of any preceding Embodiment, comprising by weight of the total composition: (a) 0.1%-2% copper-containing peptide; (b) 0.5%-10% antioxidant; and (c) 0.1%-20% cyclic oligosaccharide-based polymer.

Embodiment 71. The method of any preceding Embodiment, comprising by weight of the total composition: (a) 0.1%-2% copper-containing peptide; (b) 0.5%-10% carnosine; and (c) 0.1%-20% cyclodextrin.

Embodiment 72. The method of any preceding Embodiment, comprising by weight of the total composition: (a)

0.1%-2% GHK-Cu peptide; (b) 0.5%-10% L-carnosine; and (c) 0.1%-20% gamma cyclodextrin.

Embodiment 73. The method of any preceding Embodiment, further comprising at least one pharmaceutically acceptable carrier or excipient.

Embodiment 74. The method of any preceding Embodiment, wherein the composition is delivered by a patch, a cream, an ointment, a powder, an aerosol spray, or a hydrogel.

Embodiment 75. The method of any preceding Embodiment, wherein the composition is effective to treat a wound or inflammatory condition of the skin.

Embodiment 76. The method of any preceding Embodiment, wherein the inflammatory condition of the skin is eczema, rosacea, or combination thereof.

Embodiment 77. A kit for healing a wound and/or treating an inflammatory skin condition, the kit comprising the composition of any preceding Embodiment and instructions for use thereof.

Embodiment 78. A kit for altering gene expression of a skin cell in a human subject, the kit comprising the composition of any preceding Embodiment and instructions for use thereof.

Embodiment 79. The composition of any preceding Embodiment, wherein the composition comprises a topical formulation suitable for application to the body surface selected from the group consisting of a cream, lotion, spray, solution, gel, ointment, paste, plaster, paint, bioadhesive, suspension, and emulsion.

Embodiment 80. The composition of any preceding Embodiment, wherein the composition comprises one or more of sunscreen, lotion, balm, shampoo, and moisturizer.

Embodiment 81. The composition of any preceding Embodiment, wherein the composition comprises one or more of sunscreen, lotion, balm, shampoo, and moisturizer.

Embodiment 82. The composition of any preceding Embodiment, comprising GHK peptide, Carnosine, Gamma-Cyclodextrin, Glycerin, Propanediol, Phenoxyethanol, and ethylhexylglycerin.

Embodiment 83. The composition of any preceding Embodiment, comprising GHK peptide, Carnosine, Gamma-Cyclodextrin, Glycerin, Propanediol, Phenoxyethanol, and ethylhexylglycerin.

Embodiment 84. The method of any preceding Embodiment, wherein the composition comprises GHK peptide, Carnosine, Gamma-Cyclodextrin, Glycerin, Propanediol, Phenoxyethanol, and ethylhexylglycerin.

Embodiment 85. The method of any preceding Embodiment, wherein the composition comprises GHK peptide, Carnosine, Gamma-Cyclodextrin, Glycerin, Propanediol, Phenoxyethanol, and ethylhexylglycerin.

Embodiment 86. The composition of any preceding Embodiment, comprising 0.4% GHK peptide, 4% Carnosine, 1% Gamma-Cyclodextrin, 1% Citric acid, 2% Glycerin, 10% Propanediol, 0.7% Phenoxyethanol, 0.1% ethylhexylglycerin, and 1% HA.

Embodiment 87. The composition of any preceding Embodiment, comprising 0.4% GHK peptide, 4% Carnosine, 1% Gamma-Cyclodextrin, 1% Citric acid, 2% Glycerin, 10% Propanediol, 0.7% Phenoxyethanol, 0.1% ethylhexylglycerin, and 1% HA.

Embodiment 88. The method of any preceding Embodiment, wherein the composition comprises 0.4% GHK peptide, 4% Carnosine, 1% Gamma-Cyclodextrin, 1% Citric acid, 2% Glycerin, 10% Propanediol, 0.7% Phenoxyethanol, 0.1% ethylhexylglycerin, and 1% HA.

Embodiment 89. The method of any preceding Embodiment, wherein the composition comprises 0.4% GHK peptide, 4% Carnosine, 1% Gamma-Cyclodextrin, 1% Citric acid, 2% Glycerin, 10% Propanediol, 0.7% Phenoxyethanol, 0.1% ethylhexylglycerin, and 1% HA.

Embodiment 90. The composition of any preceding Embodiment, comprising 0.2% GHK peptide, 2% Carnosine, 1% Gamma-Cyclodextrin, 0.5% Citric acid, 2% Glycerin, 10% Propanediol, 0.7% Phenoxyethanol, 0.1% ethylhexylglycerin, 1% HA.

Embodiment 91. The composition of any preceding Embodiment, comprising 0.2% GHK peptide, 2% Carnosine, 1% Gamma-Cyclodextrin, 0.5% Citric acid, 2% Glycerin, 10% Propanediol, 0.7% Phenoxyethanol, 0.1% ethylhexylglycerin, 1% HA.

Embodiment 92. The method of any preceding Embodiment, wherein the composition comprises 0.2% GHK peptide, 2% Carnosine, 1% Gamma-Cyclodextrin, 0.5% Citric acid, 2% Glycerin, 10% Propanediol, 0.7% Phenoxyethanol, 0.1% ethylhexylglycerin, 1% HA.

Embodiment 93. The method of any preceding Embodiment, wherein the composition comprises 0.2% GHK peptide, 2% Carnosine, 1% Gamma-Cyclodextrin, 0.5% Citric acid, 2% Glycerin, 10% Propanediol, 0.7% Phenoxyethanol, 0.1% ethylhexylglycerin, 1% HA.

Embodiment 94. The composition or method of any preceding embodiment comprising 0.2-0.4% GHK peptide, 2-4% Carnosine, 1% Gamma-Cyclodextrin, 0.5-1% Citric acid, 2% Glycerin, 10% Propanediol, 0.7% Phenoxyethanol, 0.1% ethylhexylglycerin, and 1% HA.

What is claimed:

1. A composition for use in healing a wound and/or treating an inflammatory skin condition comprising:
   (a) a glycyl-L-histidyl-L-lysine copper (GHK-Cu) peptide;
   (b) one or more of L-carnosine, D-carnosine, acetyl-carnosine; and
   (c) cyclodextrin,
   wherein the GHK-Cu peptide and the one or more of L-carnosine, D-carnosine, acetyl-carnosine form a complex and the complex is entrapped by cyclodextrin.

2. The composition of claim 1, wherein the cyclodextrin is selected from the group consisting of alpha cyclodextrin, beta cyclodextrin, gamma cyclodextrin, 2-hydroxypropyl-β-cyclodextrin, β-cyclodextrin sulfobutylether, a derivative thereof, or a combination thereof.

3. The composition of claim 1, wherein the composition has a pH between 5.5 and 7.3.

4. The composition of claim 1, comprising by weight of the total composition: (a) 0.1%-2% GHK-Cu; (b) 0.5%-10% one or more of L-carnosine, D-carnosine, acetyl-carnosine; and (c) 0.1%-20% cyclodextrin.

5. The composition of claim 1, comprising 0.2-0.4% GHK-Cu peptide, 2-4% one or more of L-carnosine, D-carnosine, acetyl-carnosine, 1% Gamma-Cyclodextrin, 0.5-1% Citric acid, 2% Glycerin, 10% Propanediol, 0.7% Phenoxyethanol, 0.1% ethylhexylglycerin, and 1% hyaluronic acid (HA).

6. The composition of claim 1, wherein the composition is a patch, a cream, an ointment, a powder, an aerosol spray, or a hydrogel.

7. A composition for altering gene expression of a skin cell in a human subject comprising:
   (a) a glycyl-L-histidyl-L-lysine copper (GHK-Cu) peptide;
   (b) one or more of L-carnosine, D-carnosine, acetyl-carnosine; and (c) cyclodextrin, wherein the GHK-Cu peptide and the one or more of L-carnosine, D-carnosine, acetyl-carnosine form a complex and the complex is entrapped by cyclodextrin; and wherein the composition is effective to increase the gene expression of one or more of the genes hCOL1A2, hEGF-1, hMMP-1, hELN, hFLG, and hIGF-1.

8. The composition of claim 7, wherein the cyclodextrin is selected from the group consisting of alpha cyclodextrin, beta cyclodextrin, gamma cyclodextrin, 2-hydroxypropyl-β-cyclodextrin, β-cyclodextrin sulfobutylether, a derivative thereof, or a combination thereof.

9. The composition of claim 7, wherein the composition has a pH between 5.5 and 7.3.

10. The composition of claim 7, comprising by weight of the total composition: (a) 0.1%-2% GHK-Cu; (b) 0.5%-10% one or more of L-carnosine, D-carnosine, acetyl-carnosine; and (c) 0.1%-20% cyclic oligosaccharide-based polymer.

11. The composition of claim 7, wherein the composition is delivered by a patch, a cream, an ointment, a powder, an aerosol spray, or a hydrogel.

12. The composition of claim 7, wherein the composition comprises a topical formulation suitable for application to the body surface selected from the group consisting of a cream, lotion, spray, solution, gel, ointment, paste, plaster, paint, bioadhesive, suspension, and emulsion.

13. The composition of claim 7, comprising 0.2-0.4% GHK-Cu peptide, 2-4% one or more of L-carnosine, D-carnosine, acetyl-carnosine, 1% Gamma-Cyclodextrin, 0.5-1% Citric acid, 2% Glycerin, 10% Propanediol, 0.7% Phenoxyethanol, 0.1% ethylhexylglycerin, and 1% hyaluronic acid (HA).

14. A method for healing a wound and/or treating an inflammatory skin condition in a subject comprising administering to the subject in need thereof a therapeutically effective amount of a composition comprising:

(a) a glycyl-L-histidyl-L-lysine copper (GHK-Cu) peptide;

(b) one or more of L-carnosine, D-carnosine, acetyl-carnosine; and (c) cyclodextrin, wherein the GHK-Cu peptide and the one or more of L-carnosine, D-carnosine, acetyl-carnosine form a complex and the complex is entrapped by cyclodextrin.

15. The method of claim 14, wherein the cyclodextrin is selected from the group consisting of alpha cyclodextrin, beta cyclodextrin, gamma cyclodextrin, 2-hydroxypropyl-β-cyclodextrin, β-cyclodextrin sulfobutylether, a derivative thereof, or a combination thereof.

16. The method of claim 14, wherein the composition comprises by weight of the total composition: (a) 0.1%-2% GHK-Cu; (b) 0.5%-10% one or more of L-carnosine, D-carnosine, acetyl-carnosine; and (c) 0.1%-20% cyclodextrin.

17. The method of claim 14, wherein the composition is a patch, a cream, an ointment, a powder, an aerosol spray, or a hydrogel.

18. The method of claim 14, wherein the wound is a bed sore, an incision, an excision, a laceration, an abrasion, a puncture or a penetrating wound, a surgical wound, a contusion, a hematoma, a crushing injury, a burn ulcer, an acne scar or a shingles rash.

19. A method for altering gene expression of a human skin cell in a human subject comprising the steps of contacting the human skin cell with a composition comprising:

(a) a glycyl-L-histidyl-L-lysine copper (GHK-Cu) peptide;

(b) one or more of L-carnosine, D-carnosine, acetyl-carnosine; and (c) cyclodextrin, wherein the GHK-Cu peptide and the one or more of L-carnosine, D-carnosine, acetyl-carnosine form a complex and the complex is entrapped by cyclodextrin; and wherein the gene expression is one or more of the genes hCOL1A2, hEGF-1, hMMP-1, hELN, hFLG, and hIGF-1.

20. The method of claim 19, wherein the cyclodextrin is selected from the group consisting of alpha cyclodextrin, beta cyclodextrin, gamma cyclodextrin, 2-hydroxypropyl-β-cyclodextrin, β-cyclodextrin sulfobutylether, a derivative thereof, or a combination thereof.

21. The method of claim 19, comprising by weight of the total composition: (a) 0.1%-2% GHK-Cu; (b) 0.5%-10% one or more of L-carnosine, D-carnosine, acetyl-carnosine; and (c) 0.1%-20% cyclodextrin.

* * * * *